US007939551B2

(12) United States Patent
Jaen et al.

(10) Patent No.: US 7,939,551 B2
(45) Date of Patent: *May 10, 2011

(54) COMBINATION THERAPEUTIC COMPOSITIONS

(75) Inventors: Juan C. Jaen, Burlingame, CA (US); Jin-Long Chen, Hillsborough, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/258,817

(22) Filed: Oct. 26, 2005

(65) Prior Publication Data

US 2006/0035928 A1 Feb. 16, 2006

Related U.S. Application Data

(63) Continuation of application No. 10/456,932, filed on Jun. 5, 2003, now abandoned, which is a continuation of application No. 09/847,887, filed on May 2, 2001, now Pat. No. 6,653,332.

(60) Provisional application No. 60/201,613, filed on May 3, 2000.

(51) Int. Cl.
 A61K 31/44 (2006.01)
 A61K 31/70 (2006.01)
 A61K 31/425 (2006.01)
 A61K 31/155 (2006.01)
(52) U.S. Cl. .......... 514/347; 514/35; 514/369; 514/635; 514/866
(58) Field of Classification Search .................. 514/347, 514/35, 369, 635, 866
 See application file for complete search history.

(56) References Cited

U.S. PATENT DOCUMENTS

| | | | |
|---|---|---|---|
| 2,407,309 A | 9/1946 | Lott et al. | |
| 3,033,870 A | 5/1962 | Druey et al. | |
| 3,034,955 A | 5/1962 | Frick et al. | |
| 3,174,901 A * | 3/1965 | Sterne | 514/635 |
| 3,669,966 A * | 6/1972 | Ambrogi et al. | 544/406 |
| 3,674,843 A | 7/1972 | Shen et al. | |
| 3,686,192 A | 8/1972 | Moore et al. | |
| 4,003,734 A | 1/1977 | Johnston | |
| 4,013,621 A | 3/1977 | Knell | |
| 4,061,642 A | 12/1977 | Fleckenstein et al. | |
| 4,062,950 A * | 12/1977 | Frommer et al. | 514/35 |
| 4,218,237 A | 8/1980 | Nishiyama et al. | |
| 4,248,619 A | 2/1981 | Serban et al. | |
| 4,289,876 A | 9/1981 | Algieri et al. | |
| 4,499,304 A | 2/1985 | Gabrielsen et al. | |
| 4,549,901 A | 10/1985 | James | |
| 4,565,568 A | 1/1986 | Johnston et al. | |
| 4,572,912 A * | 2/1986 | Yoshioka et al. | 514/369 |
| 4,577,028 A | 3/1986 | Martin et al. | |
| 4,670,045 A | 6/1987 | Ehr et al. | |
| 4,731,090 A | 3/1988 | Boger et al. | |
| 4,756,739 A | 7/1988 | Fuss et al. | |
| 4,851,419 A | 7/1989 | Cox | |
| 4,866,079 A | 9/1989 | Boger et al. | |
| 4,900,751 A | 2/1990 | Cox | |
| 4,946,854 A | 8/1990 | Maienfisch et al. | |
| 4,952,235 A | 8/1990 | Andree et al. | |
| 4,987,141 A | 1/1991 | Bushell et al. | |
| 5,008,276 A | 4/1991 | Clough et al. | |
| 5,070,096 A | 12/1991 | Mohrs et al. | |
| 5,081,125 A | 1/1992 | Maienfisch et al. | |
| 5,093,340 A | 3/1992 | Mohrs et al. | |
| 5,143,937 A | 9/1992 | Lang et al. | |
| 5,151,428 A | 9/1992 | Sakamoto et al. | |
| 5,202,336 A | 4/1993 | Mohrs et al. | |
| 5,204,354 A | 4/1993 | Chakravarty et al. | |
| 5,250,549 A | 10/1993 | Yoshino et al. | |
| 5,304,532 A | 4/1994 | Munro et al. | |
| 5,360,810 A | 11/1994 | Hayase et al. | |
| 5,444,036 A | 8/1995 | Iwasaki et al. | |
| 5,514,696 A | 5/1996 | Murugesan et al. | |
| 5,545,669 A | 8/1996 | Adams et al. | |
| 5,610,320 A | 3/1997 | Yoshino et al. | |
| 5,624,937 A | 4/1997 | Reel et al. | |
| 5,643,914 A | 7/1997 | Daines | |
| 5,684,195 A | 11/1997 | Huang et al. | |
| 5,716,993 A | 2/1998 | Ozaki et al. | |
| 5,780,483 A | 7/1998 | Widdowson et al. | |
| 5,814,646 A | 9/1998 | Heinz | |
| 5,880,136 A | 3/1999 | Duggan et al. | |
| 5,990,126 A | 11/1999 | Park | |

(Continued)

FOREIGN PATENT DOCUMENTS

CH    592 411    10/1977

(Continued)

OTHER PUBLICATIONS

Http://www.en.wikipedia.org/wiki/Biguanide (2007).*
Http://www.en.wikipedia.org/wiki/Troglitazone (2007).*
Adams, B. et al., 1953, "Quinone Imides. XXV. Addition of Mercaptans to p-Quinonedibenzenesulfonimide," The Notes Chemical Laboratory, University of Illinois, Feb. 5, 1953, vol. 2:663-665.
Badilescu, 1967, "Synthesis of Some N-Aryl- and N, N-dislkyl-p-chlorobenzenesulfonamides," Chemical Abstracts, vol. 67(9):4076. Abstract No. 4316y.

(Continued)

Primary Examiner — Kevin Weddington
(74) Attorney, Agent, or Firm — Jones Day

(57) ABSTRACT

The present invention provides pharmaceutical compositions and methods for the treatment of diabetes mellitus using combination therapy. The compositions relate to a compound of Formula I and an antidiabetic agent such as sulfonylureas, biguanides, glitazones, α-glucosidase inhibitors, potassium channel antagonists, aldose reductase inhibitors, glucagon antagonists, activators of RXR, insulin therapy or other anti-obesity agent. The methods include the administration of the combination of compound of Formula I with antidiabetic agent where the two components are delivered in a simultaneous manner, where the compound of Formula I is administered first, followed by the antidiabetic agent, as well as wherein the antidiabetic agent is delivered first followed by the compound of Formula I.

26 Claims, 7 Drawing Sheets

U.S. PATENT DOCUMENTS

| | | | |
|---|---|---|---|
| 6,022,897 | A | 2/2000 | Evans et al. |
| 6,028,052 | A | 2/2000 | Cesario et al. |
| 6,200,995 | B1 * | 3/2001 | De la Brouse-Elwood et al. ............................ 514/347 |
| 6,214,850 | B1 | 4/2001 | Evans et al. |
| 6,262,112 | B1 | 7/2001 | Mittendorf et al. |
| 6,294,559 | B1 | 9/2001 | Smith |
| 6,348,474 | B1 | 2/2002 | Kayakiri et al. |
| 6,353,011 | B1 | 3/2002 | Pershadsingh et al. |
| 6,369,075 | B1 | 4/2002 | Ruggeri et al. |
| 6,376,512 | B1 | 4/2002 | Jayyosi et al. |
| 6,403,607 | B1 | 6/2002 | Hidaka et al. |
| 6,469,054 | B1 | 10/2002 | Mittendorf et al. |
| 6,472,779 | B2 | 10/2002 | Hwang et al. |
| 6,545,050 | B1 | 4/2003 | Mittendorf et al. |
| 6,573,278 | B2 | 6/2003 | Mittendorf et al. |
| 6,583,157 | B2 | 6/2003 | McGee et al. |
| 6,586,475 | B1 | 7/2003 | Kato et al. |
| 6,620,827 | B2 | 9/2003 | De la Brouse-Elwood et al. |
| 6,653,309 | B1 | 11/2003 | Saunders et al. |
| 6,653,332 | B2 * | 11/2003 | Jaen et al. ....................... 514/347 |
| 6,677,488 | B2 * | 1/2004 | Reitz et al. ........................ 568/28 |
| 6,770,648 | B2 | 8/2004 | McGee et al. |
| 7,041,691 | B1 * | 5/2006 | McGee et al. ................ 514/367 |
| 7,132,546 | B2 | 11/2006 | Kato et al. |
| 7,223,761 | B2 | 5/2007 | Kruk et al. |
| 7,439,242 | B2 | 10/2008 | Houze et al. |
| 7,601,841 | B2 | 10/2009 | McGee et al. |
| 7,626,033 | B2 | 12/2009 | McGee et al. |
| 2001/0028200 | A1 | 10/2001 | Hwang et al. |
| 2003/0088103 | A1 | 5/2003 | Houze et al. |
| 2003/0171399 | A1 | 9/2003 | McGee et al. |
| 2004/0048891 | A1 | 3/2004 | Kato et al. |
| 2004/0176409 | A1 | 9/2004 | McGee et al. |
| 2004/0248882 | A1 | 12/2004 | McGee et al. |
| 2004/0259918 | A1 | 12/2004 | Jaen et al. |

FOREIGN PATENT DOCUMENTS

| | | |
|---|---|---|
| DE | 3632329 | 3/1988 |
| EP | 069585 | 1/1983 |
| EP | 0148730 | 7/1985 |
| EP | 0 261 539 A2 | 9/1987 |
| EP | 0306222 | 3/1989 |
| EP | 0472053 | 2/1992 |
| EP | 0749751 | 12/1996 |
| EP | 0778267 | 6/1997 |
| EP | 0855391 | 7/1998 |
| GB | 2373725 | 10/2002 |
| JP | 55-79369 | 6/1980 |
| JP | 64-6245 | 1/1989 |
| JP | 9-255656 | 9/1997 |
| WO | WO 95/01326 | 1/1995 |
| WO | WO 95/33461 | 12/1995 |
| WO | WO 95/33462 | 12/1995 |
| WO | WO 96/09294 | 3/1996 |
| WO | WO 96/15118 | 5/1996 |
| WO | WO 97/00857 | 1/1997 |
| WO | WO 97/30677 | 8/1997 |
| WO | WO 97/30677 A1 | 8/1997 |
| WO | WO 97/31907 | 9/1997 |
| WO | WO 97/36579 | 10/1997 |
| WO | WO 98/02437 | 1/1998 |
| WO | WO 98/16503 | 4/1998 |
| WO | WO 98/27081 | 6/1998 |
| WO | WO 98/37061 A1 | 8/1998 |
| WO | WO 98/50029 | 11/1998 |
| WO | WO 98/50030 | 11/1998 |
| WO | WO 99/00372 A1 | 1/1999 |
| WO | WO 99/06378 | 2/1999 |
| WO | WO 99/10320 | 3/1999 |
| WO | WO 99/20275 | 4/1999 |
| WO | WO 99/24404 | 5/1999 |
| WO | WO 99/32465 | 7/1999 |
| WO | WO 99/38845 | 8/1999 |
| WO | WO 99/50237 A1 | 10/1999 |
| WO | WO 99/55663 | 11/1999 |
| WO | WO 00/10967 A1 | 3/2000 |
| WO | WO 00/12073 | 3/2000 |
| WO | WO 00/12623 | 3/2000 |
| WO | WO 00/17202 | 3/2000 |
| WO | WO 00/31021 A1 | 6/2000 |
| WO | WO 00/10968 A3 | 11/2000 |
| WO | WO 01/00579 | 1/2001 |
| WO | WO 01/30343 | 5/2001 |
| WO | WO 01/60807 | 8/2001 |
| WO | WO 01/70723 | 9/2001 |
| WO | WO 01/82916 | 11/2001 |
| WO | WO 01/83427 | 11/2001 |
| WO | WO 01/87860 | 11/2001 |
| WO | WO 01/87861 | 11/2001 |
| WO | WO 01/87862 | 11/2001 |
| WO | WO 01/95906 | 12/2001 |
| WO | WO 02/00611 | 1/2002 |
| WO | WO 02/00633 A1 | 1/2002 |
| WO | WO 02/08188 | 1/2002 |
| WO | WO 02/13812 | 2/2002 |
| WO | WO 02/13864 | 2/2002 |
| WO | WO 02/14291 | 2/2002 |
| WO | WO 02/17901 | 3/2002 |
| WO | WO 02/18355 | 3/2002 |
| WO | WO 02/26729 | 4/2002 |
| WO | WO 02/26737 | 4/2002 |
| WO | WO 02/28832 | 4/2002 |
| WO | WO 02/28857 | 4/2002 |
| WO | WO 02/30860 | 4/2002 |
| WO | WO 02/30863 | 4/2002 |
| WO | WO 02/30884 | 4/2002 |
| WO | WO 02/30895 | 4/2002 |
| WO | WO 02/40020 | 5/2002 |
| WO | WO 02/46161 | 6/2002 |
| WO | WO 02/49626 | 6/2002 |
| WO | WO 02/051397 | 7/2002 |
| WO | WO 02/051397 A1 | 7/2002 |
| WO | WO 02/051820 | 7/2002 |
| WO | WO 02/053546 | 7/2002 |
| WO | WO 02/059098 | 8/2002 |
| WO | WO 02/060434 | 8/2002 |
| WO | WO 02/062772 | 8/2002 |
| WO | WO 02/062774 | 8/2002 |
| WO | WO 02/062798 A3 | 8/2002 |
| WO | WO 02/062799 | 8/2002 |
| WO | WO 02/064094 | 8/2002 |
| WO | WO 02/066028 | 8/2002 |
| WO | WO 02/072003 | 9/2002 |
| WO | WO 02/074291 | 9/2002 |
| WO | WO 02/080913 | 10/2002 |
| WO | WO 02/081454 | 10/2002 |
| WO | WO 02/090882 | 11/2002 |
| WO | WO 02/092084 | 11/2002 |
| WO | WO 02/092590 | 11/2002 |
| WO | WO 2005/033074 A2 | 4/2005 |

OTHER PUBLICATIONS

Baguley et al., 1988, "Relationship Between the Structure of Analogs of Amsacrine and Their Degree of Cross-Resistance to Adriamycin-Resistant p388 Leukaemia Cells," Database Accession No. 108:179602; Database Chemabs 'Online!, RN 106831-10-1 CAPLUS, Eur. J. Cancer Clin. Oncol., 24(2):205-210, Abstract.

Burmistrov et al., 1990, "Reaction of Unsymmetrical N1, N4-Disubstituted 1,4-Benzoquinone Diimines with Hydrogen Chloride," Database Accession No. 115:8165, Database Chemabs 'Online!, RNs 98187-76-9 CAPLUS, 134284-40-5 CAPLUS, Zh. Org. Khim, 26(9):1995-1998, Abstract.

Burmistrov et al., 1994, "Mechanism of Reaction of Quinonediimines with Hydrogen Chloride," Database Accession No. 122:132338, Database Chemabs 'Online!, RN 134284-40-5 CAPLUS, Zh. Org. Khim, 30(5):744-747, Abstract.

Cain et al., 1974, "Potential Antitumor Agents. 14. Acridylmethanesulfonanilides," J. Med Chem., vol. 17(9):922-930.

Chaturvedi and Goyal, 1984, "Antibacterial Studies of 7-(α-Substituted Sulphonamido) Methyl- and 7-(α-Substituted Sulphonamido)Phenyl-8-Hydroxyquinolines," Journal of the Indian Chemical Soc., vol. 61(2):175-176. (Abstract Chem. Abstract Accession No. 101:87311).

Collins et al., 1998, "N-(2-Benzoylphenyl)-L-tyrosine PPARγ Agonists. 2. Structure-Activity Relationship and Optimization of the Phenyl Alkyl Ether Moiety," J. Med. Chem., vol. 41(25):5037-5054.
Denny et al., 1982, "Potential Antitumor Agents," Database Accession No. 96:79437, Database Chemabs 'Online!, RNs 80260-24-8 CAPLUS, 80260-26-0 CAPLUS, J. Med. Chem., 25(3):276-315 (1982), Abstract.
Dumas et al., 1999, "Synthesis and Structure-Activity Relationships of Novel Small Molecule Cathepsin D Inhibitors," Chemical abstracts, vol. 131:336969; abstract of Bio. Org. Med. Chem. Lett., vol. 9(17)2531-2536, Abstract.
Forman et al., 1995, "15-Deoxy-$\Delta^{12,14}$-Prostagladin $J_2$ is a Ligand for the Adipocyte Determination Factor PPARγ," Cell, 83:803-812.
Jiang et al., 1998, "PPAR-γ Agonists Inhibit Production of Monocyte Inflammatory Cytokines," Nature, vol. 391:82-85.
Lehmann et al., 1995, "An Antidiabetic Thiazolidinedione is a High Affinity Ligand for Peroxisome Proliferator-Activated Receptor γ (PPARγ)," J. Biol. Chem., vol. 270(22):12953-12956.
Lehmann et al., 1997, Peroxisome Proliferator-Activated Receptors α and γ Are Activated by Indomethacin and Other Non-Steroidal Anti-Infmammatory Drugs, The Journal of Biological Chemistry, vol. 272(6):3406-3410.
Misra, V., 1979, "Synthesis of New Substituted Quinolines & Study of Their Effect on the Tobacco Mosaic Virus," Indian Journal of Chemistry, vol. 18B(3):262-264.
Mysyk et al., 1979, "Acyl Derivatives of Arylenediamines," Database Accession No. 92:163637, Database Chemabs 'Online!, RN 73320-75-9 CAPLUS, Zh. Org. Khim, 15(12):2499-2502, Abstract.
Pieper et al., 1989, "Preparation and Biological Activity of New Substituted Antimalarial Diaminodiphcnylsulfones," Database Accession No. 112:138679, Database Chemabs 'Online!, RN 101513-48-8 CAPLUS, Arzneim-Forsch, 39(9):1073-1080, Abstract.
Ricote et al., 1998, "The Peroxisome Proliferator-Activated Receptor-γ is a Negative Regulator of Macrophage Activation," Nature, vol. 391:79-82.
Sarul et al., 1985, "Quinone Imines and Quinoidal Macrocycles.," Database Accession No. 103:123106, Database Chemabs 'Online!, RN 98187-77-0 CAPLUS, Latv. Psr Zinat. Akad. Vestis, Kim. Ser., 2:225-228, Abstract.
Sebe et al., 1992, "Synthesis of Anthraquinone Dyes Derived from 1-Amino-4-Bromoanthraquinone-2-Sulfonic Acid," Database Accession No. 117:214517, Database Chemabs 'Online!, RNs 144206-02-0 CAPLUS, 144232-65-5 CAPLUS, Rev. Chim, 43(5-6_:222-225, Abstract.
Shah, A.R., 1987, "Quinaldine Sulphonamide Derivatives," Journal of Institution of Chemists, vol. 59:257-258.
Spiegelman, B.M., 1998, "PPAR-γ: Adipogenic Regulator and Thiazolidinedione Receptor," Diabetes, vol. 47:507-514.
Willson et al., 1996, "The Structure-Activity Relationship between Peroxisome Proliferator-Activated Receptor γ Agonism and the Antihyperglycemic Activity of Thiazolidinediones," J. Med. Chem, vol. 39:665-668.
Willson et al., 2000, "The PPARs: From Orphan Receptors to Drug Discovery," Journal of Medicinal Chemistry, vol. 43(4):527-550.
Windholz et al., 1983, The Merck Index, 10th Ed., Abstract 5792; pp. 849-850.
Wollweber et al., 1984, "2-(Guanidino)Anilides and Related Compounds. Synthesis and Anthelmintic Activity," Database Accession No. 101:151540, Database Chemabs 'Online!, RN 92114-63-1 CAPLUS, Arzneim-Forsch, vol. 34(5):531-542, Abstract.
Zaitseva et al., 1976, "Synthesis of Aromatic Bis-(O-Cyano)Diamines," Database Accession No. 86:43377, Database Chemabs 'Online!, RN 61381-98-4 CAPLUS, Zh. Org. Khim, 12(9):1987-1992, Abstract.
AU—Australian Patent Office Examination Report dated Jul. 8, 2003, for Application No. 60643/00.
Au—Australian patent office Examination Report dated Jul. 27, 2004, for Application No. 60643/00.
CN—Intellectual Property Office of the People's Republic of China, Office action dated Feb. 20, 2004, for Application No. 01812017.2, filed Jun. 27, 2001.
EPO—European Official Action dated Oct. 8, 2007, in EP Patent Application No. 00 946 961.0-2101.
IPOS—Intellectual Property Office of Singapore, Examination Report dated Oct. 4, 2007, for Singapore Patent Application No. 200403480-7, based on the attached Examination Report of the Australian Patent Office, dated Sep. 12, 2007.
ISA/EP International Search Report, dated May 16, 2002, for International Application No. PCT/US2001/14393, filed May 2, 2001.
IPEA/EP International Preliminary Examination Report, dated Nov. 13, 2002, for International Application No. PCT/US2001/14393.
ISA/EP International Search Report, dated May 7, 1999, for International Application No. PCT/US1999/01147, filed Jan. 20, 1999.
IPEA/EP PCT Written Opinion of the International Preliminary Examining Authority, dated Oct. 8, 1999, for International Application No. PCT/US1999/01147, filed Jan. 20, 1999.
IPEA/RU Examination Report dated Mar. 14, 2005, for Application No. 2002/02750.
IPEA/RU Examination Report dated Aug. 18, 2008, for Application No. 2002/02750.
JPO—Japanese Official Action dated Jun. 24, 2008, in JP Patent Application No. 2001-506989.
JPO—Japanese Official Action dated Jun. 24, 2008, in JP Patent Application No. 2000-530082.
NO—Norway Patent Office Official action dated May 10, 2007, for Norwegian Patent Application No. 20026156, based on the attached English language Examination Report of the Russian Preliminary Examining Authority, dated Mar. 14, 2005.
U.S.P.T.O. Non-Final Office action dated Jun. 15, 2005, issued in U.S. Appl. No. 10/719,997, filed Nov. 20, 2003.
U.S.P.T.O. Non-Final Office action dated Feb. 28, 2006, issued in U.S. Appl. No. 10/719,997, filed Nov. 20, 2003.
U.S.P.T.O. Non-Final Office action dated Nov. 20, 2006, issued in U.S. Appl. No. 10/719,997, filed Nov. 20, 2003.
U.S.P.T.O. Non-Final Office action dated Jul. 23, 2007, issued in U.S. Appl. No. 10/719,997, filed Nov. 20, 2003.
U.S.P.T.O. Non-Final Office action dated Jul. 28, 2008, issued in U.S. Appl. No. 10/719,997, filed Nov. 20, 2003.
U.S.P.T.O. Notice of Allowance and Fee(s) Due dated Nov. 17, 2008, issued in U.S. Appl. No. 10/719,997, filed Nov. 20, 2003.
U.S.P.T.O. Non-Final Office action dated Jun. 6, 2002; issued in U.S. Appl. No. 09/847,887, filed May 2, 2001.
U.S.P.T.O. Notice of Allowance and Fees Due dated Feb. 27, 2003; issued in U.S. Appl. No. 09/847,887, filed May 2, 2001.
U.S.P.T.O. Non-Final Office action dated Jan. 23, 2003; issued in U.S. Appl. No. 10/209,205, filed Jul. 30, 2002.
U.S.P.T.O. Notice of Allowance and Fees due dated Jun. 13, 2003; issued in U.S. Appl. No. 10/209,205, filed Jul. 30, 2002.
U.S.P.T.O. Non-Final Office action dated Nov. 12, 2004; issued in U.S. Appl. No. 10/456,932, filed Jun. 5, 2003.
U.S.P.T.O. Final Office action dated May 26, 2005; issued in U.S. Appl. No. 10/456,932, filed Jun. 5, 2003.
U.S.P.T.O. Express Abandonment Under 37 CFR 1.138 dated Dec. 16, 2005; issued in U.S. Appl. No. 10/456,932, filed Jun. 5, 2003.
U.S.P.T.O. Non-Final Office action dated Jun. 15, 2005; issued in U.S. Appl. No. 10/956,251, filed Oct. 1, 2004.
U.S.P.T.O. Mar. 23, 2006 Interview Summary dated Mar. 30, 2006; issued in U.S. Appl. No. 10/956,251, filed Oct. 1, 2004.
U.S.P.T.O. Advisory Action dated Apr. 27, 2006; issued in U.S. Appl. No. 10/956,251, filed Oct. 1, 2004.
U.S.P.T.O. Non-Final Office action dated Jun. 22, 2006; issued in U.S. Appl. No. 10/956,251, filed Oct. 1, 2004.
U.S.P.T.O. Notice of Allowance dated Jan. 22, 2007; issued in U.S. Appl. No. 10/956,251, filed Oct. 1, 2004.
Bastin et al., "Salt Selection and Optimisation Procedures for Pharmaceutical New Chemical Entities," Organic Process Research and Development, Cambridge. GB, vol. 4, No. 5, Jan. 1, 2000, pp. 427-435.
Berger, J. Biological Chemistry, vol. 274, No. 10, Mar. 1999, pp. 6718-6725.
Clark, J. Leukocyte Biology, vol. 71, Mar. 2002, pp. 388-400.
ISA, International Search Report, dated Oct. 13, 2000, for PCT/US00/18178.

ISA, International Search Report, dated Oct. 29, 2001, for PCT/US01/20756.
ISA, International Search Report and Written Opinion, dated Apr. 6, 2005, for PCT/US04/32552.
ISEA/EP, International Preliminary Examination Report, dated Aug. 3, 2001, for PCT/US00/18178.
ISEA/EP, International Preliminary Examination Report, dated Jun. 10, 2002, for PCT/US01/20756.
ISEA/EP, International Preliminary Report on Patentability, dated Apr. 3, 2006, for PCT/USO4/032552.
EPO—Supplementary European Search Report, dated Feb. 17, 2009, for European Patent Application No. EP 04 79 4053.1.
RU—Russian Office Action (with English translation), dated Feb. 26, 2009, for Russian Patent Application No. 200600701(2006050002).
AU—Australian Examiner's Report, dated Apr. 6, 2009, for Australian Patent Application No. 2004278416.
EPO—European Communication Pursuant to Article 94(3) EPC, dated Jul. 13, 2009, for European Patent Application No. EP 00 946 961.0.
CA Canadian Office Action, dated Aug. 18, 2009, for Canadian Patent Application No. 2,377,309.
CN—Intellectual Property Office of the People's Republic of China Decision of Rejection (with English translation), dated Sep. 25, 2009, for Chinese Patent Application No. 200480034669.7.
U.S.P.T.O. Non-Final Office Action, dated Apr. 19, 2007, for U.S. Appl. No. 10/123,298.
U.S.P.T.O. Non-Final Office Action, dated Feb. 15, 2002, for U.S. Appl. No. 09/741,415.
U.S.P.T.O. Non-Final Office Action, dated Jul. 29, 2002, for U.S. Appl. No. 09/741,415.
U.S.P.T.O. Final Office action, dated Mar. 11, 2009, for U.S. Appl. No. 10/810,325.
U.S.P.T.O. Issue Notification for U.S. Appl. No 10/810,325, (Nov. 11, 2009).
U.S.P.T.O. Final Office action, dated Jan. 4, 2006, for U.S. Appl. No. 10/956,251.
U.S.P.T.O. Non-final Office action, dated Dec. 3, 2001, for U.S. Appl. No. 09/606,433.
U.S.P.T.O. Restriction Requirement, dated Dec. 28, 2001, for U.S. Appl. No. 09/847,887.
U.S.P.T.O. Non-final Office action, dated Feb. 23. 2010, for U.S. Appl. No. 12/372,699.

* cited by examiner

PPARγ Agonists

| | | |
|---|---|---|
| 1. |  | TROGLITAZONE |
| 2. |  | ROSIGLITAZONE (BRL4963) |
| 3. |  | PIOGLITAZONE |
| 4. |  | JTT 501 |
| 5. |  | YM 440 (YAMANOUCHI) |
| 6. |  | CIGLITAZONE |
| 7. |  | DARGLITAZONE |
| 8. |  | ENGLITAZONE |
| 9. |  | AD-5075 (MERCK) |
| 10. |  | BM 131246 (BOEHRINGER M.) |

|    | Ra | Rb | Rc      | Rd   |
|----|----|----|---------|------|
| 1. | Cl | H  | Cl      | CH₃  |
| 2. | H  | H  | OCF₃    | H    |
| 3. | H  | H  | CN      | H    |
| 4. | H  | H  | SO₂CH₃  | H    |

|    | Ra | Rb | Rc     | Rd |
|----|----|----|--------|----|
| 5. | H  | H  | CF₃    | H  |
| 6. | Cl | H  | CF₃    | H  |
| 7. | H  | H  | COCH₃  | H  |
| 8. | H  | Cl | Cl     | H  |

|     | Ra | Rb | Rc      | Rd |
|-----|----|----|---------|----|
| 9.  | Cl | H  | Cl      | H  |
| 10. | H  | H  | SCH₃    | H  |
| 11. | H  | H  | S(O)CH₃ | H  |

|     | Ra | Rb | Rc      | Rd |
|-----|----|----|---------|----|
| 12. | Cl | H  | Cl      | H  |
| 13. | H  | H  | OCH₃    | H  |
| 14. | H  | H  | I       | H  |
| 15. | H  | H  | C(O)CH₃ | H  |
| 16. | H  | H  | CF₃     | H  |

|     | Ra | Rb | Rc  | Rd |
|-----|----|----|-----|----|
| 17. | Cl | H  | Cl  | H  |
| 18. | H  | H  | CF₃ | H  |

|     | Ra | Rb | Rc   | Rd |
|-----|----|----|------|----|
| 19. | Cl | H  | Cl   | H  |
| 20. | Cl | H  | CF₃  | H  |
| 21. | H  | H  | I    | H  |
| 22. | H  | H  | OCH₃ | H  |

| | | Ra | Rb | Rc | Rd |
|---|---|---|---|---|---|
| 23. | 3,5-dichlorophenyl | Cl | H | Cl | H |
| 24. | 3,5-difluorophenyl | H | H | CF$_3$ | H |
| 25. | 3,5-dichlorophenyl | H | H | CF$_3$ | H |
| 26. | 3,5-difluorophenyl | Cl | H | Cl | H |
| 27. | 3,5-difluorophenyl | H | H | OCH$_3$ | H |
| 28. | 3,5-dimethoxyphenyl | Cl | H | Cl | H |
| 29. | 3,5-dimethoxyphenyl | Cl | H | CF$_3$ | H |
| 30. | 3,5-dimethoxyphenyl | H | H | OCH$_3$ | H |

| | Ra | Rb | Rc | Rd |
|---|---|---|---|---|
| 31. | Cl | H | Cl | H |
| 32. | Cl | H | I | H |
| 33. | H | H | OCH$_3$ | H |

|     | Ra | Rb | Rc | Rd |
|-----|----|----|----|----|
| 34. | H  | Cl | Cl | H  |
| 35. | Cl | H  | Cl | H  |
| 36. | H  | H  | I  | H  |

|     | Ra | Rb | Rc  | Rd |
|-----|----|----|-----|----|
| 37. | H  | Cl | Cl  | H  |
| 38. | Cl | H  | Cl  | H  |
| 39. | H  | H  | I   | H  |
| 40. | Cl | H  | Cl  | Me |
| 41. | Cl | H  | CF$_3$ | H  |

|     | Ra | Rb | Rc | Rd | Re     | Rf |
|-----|----|----|----|----|--------|----|
| 42. | H  | H  | Cl | H  | CH$_3$ | Cl |
| 43. | H  | H  | Cl | H  | CF$_3$ | Cl |
| 44. | H  | H  | Cl | H  | Br     | Cl |
| 45. | H  | H  | Cl | H  | CF$_3$ | H  |

|     | Ra | Rb | Rc  | Rd |
|-----|----|----|-----|----|
| 46. | H  | Cl | Cl  | H  |
| 47. | Cl | H  | Cl  | H  |
| 48. | H  | H  | I   | H  |
| 49. | Cl | H  | CF₃ | H  |

COMBINATION THERAPEUTIC COMPOSITIONS

CROSS REFERENCE TO RELATED APPLICATIONS

This application is a continuation of U.S. patent application Ser. No. 10/456,932, filed Jun. 5, 2003, now abandoned, which is a continuation of U.S. patent application Ser. No. 09/847,887, filed May 2, 2001, now U.S. Pat. No. 6,653,332, which claims the benefit of U.S. Provisional Application No. 60/201,613, filed May 3, 2000, all of which applications are herein incorporated by reference in their entireties.

FIELD OF INVENTION

In general, the present invention relates to pharmaceutical compositions, and more particularly, to pharmaceutical compositions for the treatment of diabetes mellitus using combination therapy.

BACKGROUND OF THE INVENTION

Diabetes mellitus is a term generally used to refer to various pathological states characterized by hyperglycemia and altered metabolism of lipids, carbohydrates and proteins. These conditions are also often associated with other co-morbidities, such as obesity and an increased risk of cardiovascular disease. By some estimates, as many as 600,000 new individuals become clinically diabetic every year in the United States.

Diabetic conditions are generally classified as either insulin-dependent diabetes mellitus (IDDM, Type I diabetes) or non-insulin-dependent diabetes mellitus (NIDDM, Type II diabetes). There are also less common clinical pathologies that are associated with diabetic conditions, such as gestational maturity-onset diabetes of youth (MODY), tropical diabetes secondary to chronic pancreatis, diabetes secondary to pancreatic disease or surgery, and diabetes secondary to endocrinopathies.

Virtually all forms of diabetes are due to a decrease in the circulating concentration of insulin (insulin deficiency) and/or a decrease in the response of peripheral tissues to insulin (insulin resistance). These abnormalities lead to alterations in the metabolism of carbohydrates, lipids, ketones and amino acids, and a hyperglycemic condition. IDDM appears to have an autoimmune etiology, which results in destruction of β islet cells in the pancreas and the resulting inability to produce insulin. The etiology of NIDDM, the most prevalent form of diabetes, is more complex and possibly heterogeneous. Some loss of β-cell volume is generally noted in these patients, as well as decreased circulating levels of insulin. NIDDM patients may also suffer commonly from insulin resistance.

The best-established therapy for all IDDM and many NIDDM patients is subcutaneous insulin treatment. Additionally, insulin is used as the treatment of choice for patients with postpancreatectomy diabetes or gestational diabetes. While insulin is a key element in the control of these hyperglycemic conditions, there are a number of limitations associated with its use, including hypoglycemia, allergic reactions to insulin, lipoatrophy, lipohypertrophy, body weight gain, edema, and insulin resistance. There are a number of new forms of insulin on the market or in various stages of clinical evaluation, including new delivery systems, various recombinant forms, new routes of administration, and gene therapy. These novel forms of insulin treatments are believed to share some of the same limitations outlined above. A significant improvement in the treatment of diabetes can be achieved if insulin treatment is combined with agents that increase the insulin sensitivity of the peripheral tissues.

The concept of combination therapy is well exploited in current medical practice. Treatment of a pathology by combining two or more agents that target the same pathogen or biochemical pathway sometimes results in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect can be synergistic (the efficacy of the combination is greater than the sum of the effects of each drug given alone). In real medical practice, it is often quite difficult to determine if drug combinations are additive or synergistic.

For most diabetic patients, treatment involves some form of insulin therapy. In addition, IDDM patients may receive a biguanide (e.g., metformin) to enhance the insulin utilization by peripheral tissues. NIDDM patients are often treated with a combination of insulin, a sulfonylurea (to enhance insulin production in the pancreas) and a biguanide or glitazone (to enhance insulin sensitivity by peripheral tissues). For example, the improved utility of a glitazone in combination with a sulfonylurea was recently demonstrated in human clinical trials (see, WO 98/36755). Recently, two glitazone compounds (rosiglitazone and pioglitazone) were approved in the United States for the treatment of NIDDM patients in combination with metformin.

A variety of antidiabetic compounds are known. For example, sulfonylureas are a group of drugs that induce hypoglycemia by stimulating insulin release from the pancreas. Generally, sulfonylureas have found wide utility in the treatment of NIDDM. Their efficacy is decreased in IDDM because of the inherent inability of the patient to produce insulin. Adverse reactions to sulfonylureas occur in a fraction of patients, particularly the elderly. One of the most severe side effects is hypoglycemia and coma. Other side effects include nausea and vomiting, cholestatic jaundice, agranulocytosis, cardiovascular mortality, aplastic and hemolytic anemias, generalized hypersensitivity reactions and dermatological reactions.

Biguanides are another group of drugs, first introduced in the mid 1950's, that have shown efficacy in the treatment of hyperglycemia by mechanisms that are not well understood. The best known agents of this type include metformin, phenformin and buformin. Unlike the sulfonylureas, metformin does not induce release of insulin from the pancreas. It is thought that its effects are mediated by increasing insulin activity in peripheral tissues, reducing hepatic glucose output due to inhibition of gluconeogenesis and reducing the absorption of glucose from the intestine. Side effects associated with the use of biguanides include lactic acidosis, diarrhea, nausea, and anorexia. These agents are often given in combination with drugs that increase the output of insulin from the pancreas, such as the sulfonylureas, which sometimes results in greater efficacy and/or the ability to use lower doses of the drugs, with an improved side effect profile.

More recently, the glitazones have been introduced and are widely used in the treatment of NIDDM. These agents, also known generically as thiazolidinediones, such as troglitazone, rosiglitazone and pioglitazone, are thought to work by increasing the sensitivity of peripheral tissues, such as skeletal muscle, towards insulin. They are often used in combination with insulin or other agents, such as the sulfonylureas, that enhance the release of insulin from the pancreas. A number of side effects have been described during the clinical evaluation of these agents, including hepatotoxicity, organomegaly, edema, anemia and body weight gain. While hepatotoxicity may be the most acutely life-threatening of these conditions, it does not appear in a large percentage of the patient population. On the other hand, the increases in body weight gain associated with chronic glitazone treatment are generally perceived as worsening an already critical co-morbid condition in the majority of the diabetic patients, and may ultimately result in the loss of antidiabetic efficacy for this type of agent after chronic treatment.

α-Glucosidase inhibitors, such as acarbose, reduce intestinal absorption of starch, dextrin, and disaccharides by inhibiting the action of intestinal brush border α-glucosidase. Inhibition of this enzyme slows the absorption of carbohydrates and the rise in plasma glucose that normally follows after a meal is blunted. Acarbose has shown some benefit in IDDM and NIDDM patients, but is often associated with dose-related malabsorption, flatulence and abdominal bloating.

Other types of agents that have found limited utility in treating diabetes include potassium channel antagonists such as repaglinide, and aldose reductase inhibitors such as zopolrestat and tolrestat. Still in the experimental stage, glucagon antagonists, activators of the retinoid-X receptor (RXR), activators of PPARα, activators of PPARδ and anti-obesity agents are also being evaluated as potential antidiabetic agents.

In view of the foregoing, there remains a need in the art to provide more efficacious treatment for diabetic conditions and diabetic complications. Combination therapy treatments are needed that will reduce the amount of drugs taken, thereby decreasing side effects. The present invention fulfills these and other needs.

SUMMARY OF THE INVENTION

The present invention provides pharmaceutical compositions for the treatment of a variety of diseases, including diabetes mellitus, such as IDDM, NIDDM, gestational diabetes, juvenile diabetes, and the like, using combination therapy. In certain aspects, the pharmaceutical compositions comprise a pharmaceutically acceptable carrier with a compound of Formula I and an antidiabetic agent. Advantageously, the compositions of the present invention provide clinical advantage over the use of a single agent alone. As such, the present invention provides a composition comprising:

i) a compound of Formula I

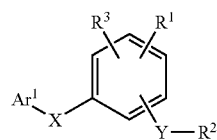

I wherein
Ar$^1$ is an aryl group; X is a divalent linkage selected from $(C_1-C_6)$alkylene, $(C_1-C_6)$alkylenoxy, $(C_1-C_6)$alkylenamino, $(C_1-C_6)$alkylene-S(O)$_k$—, —O—, —C(O)—, —N(R$^{11}$)—, —N(R$^{11}$)C(O)—, —S(O)$_k$— and a single bond, wherein R$^{11}$ is a member selected from hydrogen, $(C_1-C_8)$alkyl, $(C_1-C_8)$heteroalkyl and aryl$(C_1-C_4)$alkyl; and the subscript k is an integer of from 0 to 2; Y is a divalent linkage selected from alkylene, —O—, —C(O)—, —N(R$^{12}$)—S(O)$_m$—, —N(R$^{12}$)—S(O)$_m$—N(R$^{11}$)—, —N(R$^{12}$)C(O)—, —S(O)— and a single bond, wherein R$^{12}$ and R$^{13}$ are members independently selected from hydrogen, $(C_1-C_8)$alkyl, $(C_1-C_8)$heteroalkyl and aryl$(C_1-C_4)$alkyl; and the subscripts m and n are independently integers of from 0 to 2;

R$^1$ is a member selected from the group hydrogen, heteroalkyl, aryl, arylalkyl, halogen, cyano, nitro, $(C_1-C_8)$alkyl, $(C_1-C_8)$alkoxy, —C(O)R$^{14}$, —CO$_2$R$^{14}$—C(O)NR$^{15}$R$^{16}$, —S(O)$_p$—R$^{14}$, —S(O)$_q$—NR$^{15}$R$^{16}$, —O—C(O)—OR$^{17}$, —O—C(O)—R$^{17}$, —O—C(O)—NR$^{15}$R$^{16}$, —N(R$^{14}$)—C(O)—NR$^{15}$R$^{16}$, —N(R$^{14}$)—C(O)—R$^{17}$ and —N(R$^{14}$)—C(O)—OR$^{17}$; wherein R$^{14}$ is a member selected from hydrogen, $(C_1-C_8)$alkyl, $(C_1-C_8)$heteroalkyl, aryl and aryl$(C_1-C_4)$alkyl;

R$^{15}$ and R$^{16}$ are members independently selected from hydrogen, $(C_1-C_8)$alkyl, $(C_1-C_8)$heteroalkyl, aryl, and aryl$(C_1-C_4)$alkyl, or taken together with the nitrogen to which each is attached form a 5-, 6- or 7-membered ring;

R$^{17}$ is a member selected from alkyl, heteroalkyl, aryl and arylalkyl;

the subscript p is an integer of from 0 to 3;

the subscript q is an integer of from 1 to 2;

R$^2$ is a member selected from $(C_1-C_8)$alkyl, $(C_1-C_8)$heteroalkyl, aryl and aryl$(C_1-C_4)$alkyl;

R$^3$ is a member selected from hydrogen, halogen, cyano, nitro, $(C_1-C_8)$alkyl and $(C_1-C_8)$alkoxy;

including pharmaceutically acceptable salts of compounds of Formula I; and ii) one or more antidiabetic agents, including, but not limited to, sulfonylureas, biguanides, glitazones and other PPARγ agonists, PPARα agonists, PPARδ agonists, α-glucosidase inhibitors, potassium channel antagonists, aldose reductase inhibitors, glucagon antagonists, activators of RXR, insulin therapy or other anti-obesity agent (5), prodrugs thereof, or pharmaceutically acceptable salts of the antidiabetic agents, and a pharmaceutically acceptable carrier or diluent.

In certain aspects, the compositions of the present invention comprise a compound of Formula I formulated together with one or more antidiabetic agents. Alternatively, the compositions of the present invention comprise a compound of Formula I independently formulated with one or more antidiabetic agents i.e., separately formulated.

Suitable antidiabetic agents include, but are not limited to, sulfonylureas, biguanides, glitazones and other PPARγ agonists, α-glucosidase inhibitors, potassium channel antagonists, aldose reductase inhibitors, glucagon antagonists, activators of RXR, activators of PPARα, activators of PPARδ, insulin therapy or other anti-obesity agents. The administration of a composition comprising i) a compound of Formula I, which are PPARγ modulators and known to increase peripheral tissue sensitivity to insulin, with ii) an antidiabetic agent such as insulin therapy, or a stimulator of insulin secretion, and the like, increases the efficacy of either agent alone. In addition to increased efficacy, the combination therapy of the present invention allows for a concomitant reduction in the dose of the agents. The combination therapy of a compound of Formula I and one or more of another antidiabetic agents (e.g., biguanides, glitazones, RXR ligands, PPARγ agonists, etc.) results in a reduction in the side effects normally associated with certain antidiabetic agents.

In certain aspects, compounds of Formula I are administered in combination with antidiabetic agents that are ineffective for stimulation of insulin secretion or insulin sensitivity, such as α-glucosidase inhibitors, potassium channel antagonists, aldose reductase inhibitors, glucagon antagonists, RXR ligands, PPARα agonists, PPARδ agonists, and anti-obesity agents. Surprisingly, these types of combination therapy result in enhanced efficacy relative to the use of the single agents alone.

In another embodiment, the present invention provides methods of treating metabolic or inflammatory disorders in a host by administering a composition of the present invention. In certain preferred aspects, the method includes the administration of a composition comprising a combination of a compound of Formula I with the antidiabetic agent delivered in a simultaneous manner, such as in a single formulation. In certain other aspects, the methods of the present invention include combination therapy wherein the compound of Formula I is administered first in one formulation, followed by the antidiabetic agent in a separate formulation. The methods also include an antidiabetic agent being delivered first in one formulation, followed by a compound of Formula I in a separate formulation. The present invention includes all such methods of administration. The combination therapy is especially efficacious on conditions associated with diabetes, such as obesity, cardiovascular disease, hypercholesterolemia and other lipid disorders, peripheral neuropathies and other neurological disorders, and the like.

These and other feature and advantages will become more apparent when read with the accompanying Figures and detailed description that follow.

Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene." The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. An alkanoyl is a RCO— group.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$H_2$—$CH_2$—NH—$CH_2$—. For heteroalkylene groups, heteroatoms can also occupy either or both of the chain termini. Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl, aroyl (ArCO), heteroaroyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a heteroatom. Non-limiting examples of aryl groups include aminobenzoheteroazolyl, 2-azanaphthalenyl, bezoxazolyl, phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, 6-quinolyl, thiobenzoxazolyl, thiobenzothiazolyl and thiobenzimidazolyl. Substituents for each of the above noted aryl ring systems are selected from the group of acceptable substituents described below. The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R'', —SR', -halogen, —SiR'R''R''', —OC(O)R', —C(O)R', —CO$_2$R', CONR'R'', —OC(O)NR'R'', —NR''C(O)R', —NR'—C(O)NR''R''', —NR''C(O)$_2$R', —NH—C(NH$_2$)=NH, —NR'C(NH$_2$)=NH, —NH—C(NH$_2$)=NR', —S(O)R', S(O)$_2$R', —S(O)$_2$NR'R'', —CN and —NO$_2$ in a number ranging from zero to (2N+1), where N is the total number of carbon atoms in such radical. R', R'' and R''' each independently refer to hydrogen, unsubstituted (C$_1$-C$_8$)alkyl and heteroalkyl, unsubstituted aryl, aryl substituted with 1-3 halogens, unsubstituted alkyl, alkoxy or thioalkoxy groups, or aryl-(C$_1$-C$_4$)alkyl groups. When R' and R'' are attached to the same nitrogen atom, they can be combined with the nitrogen atom to form a 5-, 6-, or 7-membered ring. For example, —NR'R'' is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similarly, substituents for the aryl groups are varied and are selected from: -halogen, —OR', —OC(O)R', —NR'R'', —SR', —R', —CN, —NO$_2$— —CO$_2$R', —CONR'R'', —C(O)R', —OC(O)NR'R'', —NR''C(O)R', —NR''C(O)$_2$R', —NR'—C(O)NR''R''', —NH—C(NH$_2$)=NH, —NR'C(NH$_2$)=NH, —NH—C(NH$_2$)=NR', —S(O)R', —S(O)$_2$R', —S(O)$_2$NR'R'', —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R'' and R''' are independently selected from hydrogen, (C$_1$-C$_8$)alkyl and heteroalkyl, unsubstituted aryl, (unsubstituted aryl)-(C$_1$-C$_4$)alkyl, and (unsubstituted aryl)oxy-(C$_1$-C$_4$)alkyl.

Two of the substituents on adjacent atoms of the aryl ring may optionally be replaced with a substituent of the formula -T-C(O)—(CH$_2$)$_q$-U- wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula -A-(CH$_2$)$_r$-B-, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

In certain instances, aryl means two aryl groups joined by a heteroatom. These groups include diphenyl ether, phenoxy substituted 2-azanaphthalene, phenyl-thiobenzothiazole, phenyl-heterobenzoxazoles, phenyl-thiobenzoimidazoles and phenyl-heterobenzoheteroazoles (see structures IIa-IIf below).

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to, those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds that are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention can also contain unnatural proportions of atomic isotopes, stable isotopes etc., at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "prodrug" refers to compounds that are drug precursors, which, following administration, release the drug in vivo via a chemical or physiological process (e.g., a prodrug on being brought to the physiological pH is converted to the desired drug form).

"A combination amount sufficient," "an effective combination amount" "therapeutically effective combination amount" or "an effective amount of the combination of" all refer to a combined amount of both a compound of Formula I and the antidiabetic agent that is effective to ameliorate symptoms associated with diabetic diseases. As used herein, the term "combination" of compound of Formula I with an antidiabetic agent means the two compounds can be delivered in a simultaneous manner, in combination therapy wherein the compound of Formula I is administered first, followed by the antidiabetic agent, as well as wherein the antidiabetic agent is delivered first, followed by a compound of Formula I. The desired result can be either a subjective relief of a symptom(s) or an objectively identifiable improvement in the recipient of the dosage.

The terms "synergistic effective amount" refers to a combined amount of both a compound of Formula I and an antidiabetic agent that is effective to cause a synergistic effect. Synergy is a biological phenomenon in which the effectiveness of two active components in a mixture is more than additive, i.e., the effectiveness is greater than the equivalent concentration of either component alone. In certain aspects, the effectiveness of the combination therapy of a compound of Formula I and an antidiabetic agent is synergistic. Thus, synergism is a result, or function, that is more than the sum of the results, or functions of individual elements.

The term "simultaneous manner" and "combination treatment" refer to an administration protocol wherein the compound of the present invention and at least one antidiabetic agent are administered within a single 24-hour period.

DETAILED DESCRIPTION OF THE INVENTION AND PREFERRED EMBODIMENTS

Compositions

Figure 1:
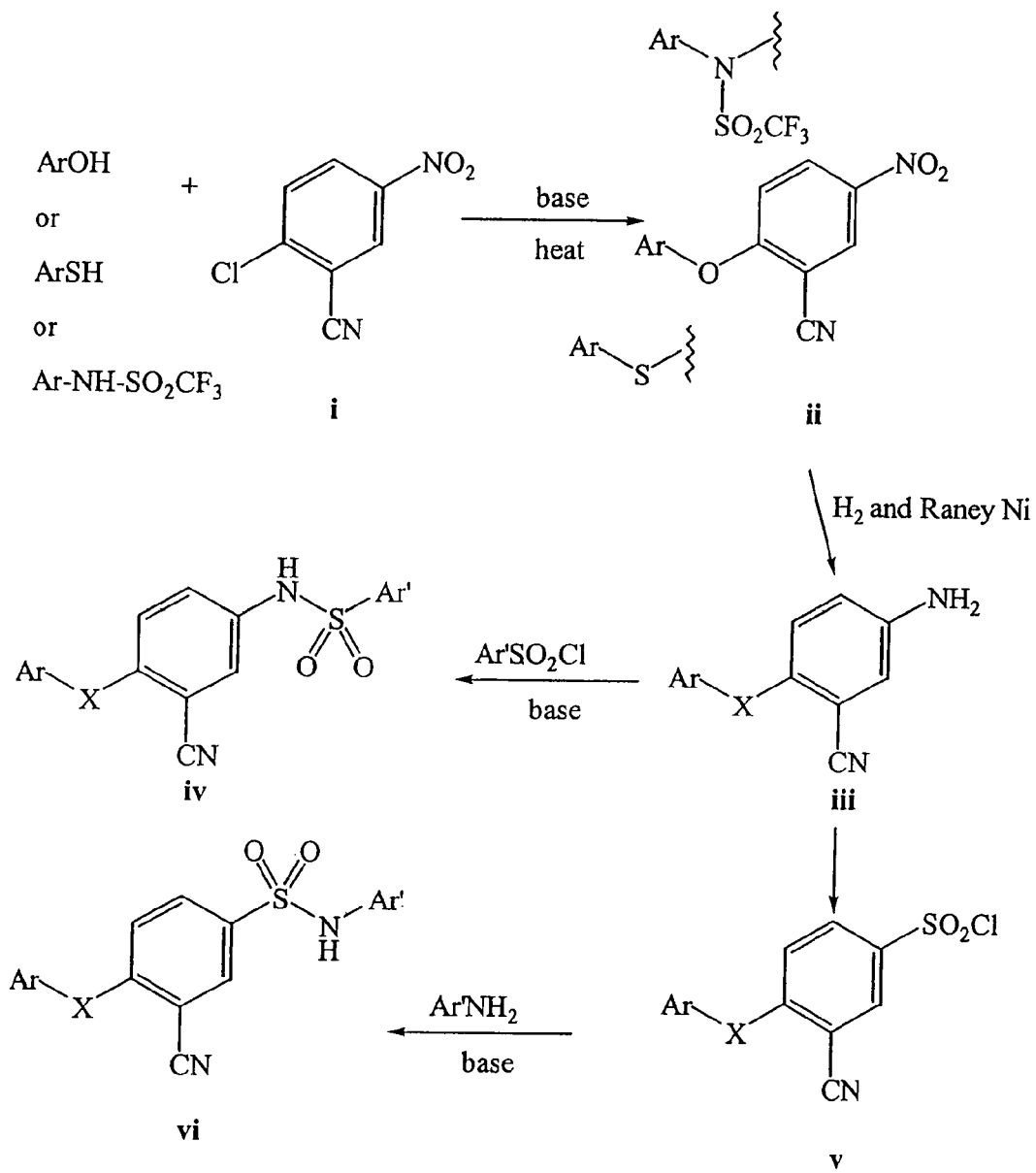
FIG. 1 shows an illustrative scheme for synthesizing compounds of Formula I.

In one embodiment, the present invention provides a pharmaceutical composition comprising (i) a compound of Formula I and (ii) an antidiabetic agent. Advantageously, the compositions of the present invention provide clinical advantage over the use of a single agent alone. As such, the present invention provides a composition comprising:
i) a compound of Formula I

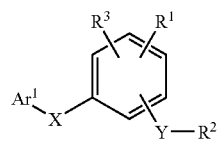

In Formula I, $Ar^1$ is a functional group including, but not limited to, an aryl group. X, in Formula I, is a divalent linkage including, but not limited to, $(C_1-C_6)$alkylene, $(C_1-C_6)$alkylenoxy, $(C_1-C_6)$alkylenamino, $(C_1-C_6)$alkylene-$S(O)_k$—, —O—, —C(O)—, —N($R^{11}$)—, —N($R^{11}$)C(O)—, —S(O)$_k$— and a single bond. $R^{11}$, in Formula I, is a functional group including, but not limited to, hydrogen, $(C_1-C_8)$alkyl, $(C_1-C_8)$heteroalkyl and aryl$(C_1-C_4)$alkyl. The index "k" is an integer of from 0 to 2 inclusive.

Y, in Formula I, is a divalent linkage including, but not limited to, alkylene, —O—, —C(O)—, —N($R^{12}$)—S(O)$_m$—, —N($R^{12}$)—S(O)$_m$—, —N($R^{13}$)—, —N($R^{12}$)C(O)—, —S(O)$_n$— and a single bond. $R^{12}$ and $R^{13}$, in Formula I, are each independent functional groups including, but not limited to, hydrogen, $(C_1-C_8)$alkyl, $(C_1-C_8)$heteroalkyl and aryl$(C_1-C_4)$alkyl. The indices "m" and "n" are each independent integers of from 0 to 2 inclusive.

In Formula I, $R^1$, is a functional group including, but not limited to, hydrogen, heteroalkyl, aryl, arylalkyl, halogen, cyano, nitro, $(C_1-C_8)$alkyl, $(C_1-C_8)$alkoxy, —C(O)$R^{14}$, —CO$_2R^{14}$ and —C(O)NR$^{15}$R$^{16}$, —S(O)$_p$—R$^{14}$, S(O)$_q$—NR$^{15}$R$^{16}$, —O—C(O)—OR$^{17}$, —O—C(O)—R$^{17}$, —O—C(O)—NR$^{15}$R$^{16}$, —N(R$^{14}$)—C(O)—NR$^{15}$R$^{16}$, —N(R$^{14}$)—C(O)—R$^{17}$ and —N(R$^{14}$)—C(O)—OR$^7$. $R^{14}$, in Formula I, is a functional group including, but not limited to, hydrogen, $(C_1-C_8)$alkyl, $(C_1-C_8)$heteroalkyl, aryl and aryl$(C_1-C_4)$alkyl. $R^{15}$ and $R^{16}$, in Formula I, are each independent functional groups including, but not limited to, hydrogen, $(C_1-C_8)$alkyl, $(C_1-C_8)$heteroalkyl, aryl, and aryl$(C_1-C_4)$alkyl. In an alternative embodiment, $R^{15}$ and $R^{16}$ taken together with the nitrogen to which each is bound form a 5-, 6- or 7-membered ring. In Formula I, $R^7$, is a functional group including, but not limited to, alkyl, heteroalkyl, aryl and arylalkyl. The index "p" is an integer of from 0 to 3 inclusive. The index "q" is an integer of from 1 to 2.

In Formula I, $R^2$, is a functional group including, but not limited to, $(C_1-C_8)$alkyl, heteroalkyl, $(C_1-C_8)$heteroalkyl, aryl and aryl$(C_1-C_4)$alkyl. $R^3$, in Formula I, is a functional group including, but not limited to hydrogen, a halogen, cyano, nitro and $(C_1-C_8)$alkoxy.

Based on the unique features of the compounds of Formula I, the combination of one of these compounds with one or more antidiabetic agents described herein provides a significant clinical advantage over the use of a single agent alone. Thus, (1) the combination of a compound of Formula I (which as activator of PPARγ, is thought to increase peripheral tissue sensitivity to insulin) with either insulin therapy, or a stimulator of insulin secretion (e.g., a sulfonylurea) increases the efficacy of either agent alone, and moreover, allows for the reduction in dosage of all agents used in the combination therapy. In addition, (2) the combination therapy between a compound of Formula I and one or more other agents that increase insulin sensitivity (e.g., biguanides, glitazones, RXR ligands, PPARγ agonists, and the like.), results in an enhanced effect between the various agents, with reduction in the side effects normally associated with these other agents. Further, (3) compounds of Formula I can be administered in combination with antidiabetic agents whose mode of action is other than stimulation of insulin secretion or insulin sensitivity (e.g., α-glucosidase inhibitors, potassium channel antagonists, aldose reductase inhibitors, glucagon antagonists, RXR ligands and anti-obesity agents). Importantly, these types of combinations result in enhanced efficacy relative to the use of a single agent alone. In addition, the present invention includes (4) a combination treatment comprising a compound of Formula I in combination with agents aimed at treating any one of the conditions often associated with diabetes, such as obesity, cardiovascular disease, hypercholesterolemia and other lipid disorders, peripheral neuropathies and other neurological disorders.

The compounds of Formula I are known to interact with the peroxisome proliferator-activated receptor gamma (PPARγ) protein, a member of the nuclear receptor family. These compounds possess the ability to bind to PPARγ with high affinity while inducing only a partial functional activation of the receptor's potential transcriptional activity. This property is sometimes described as "partial agonism". The exact potency and intrinsic agonist activity of each compound of Formula I is a function of the compound's structure in a relatively predictable manner.

Compounds of Formula I, as partial PPARγ agonists, have been shown, in diabetic animal models, to possess the anti-diabetic efficacy of the glitazones, but with a decreased propensity to induce body weight gain. One of the major side effects of glitazones (e.g., troglitazone, rosiglitazone and pioglitazone) is their obesity-inducing potential. This effect is thought to be related to their full activation of PPARγ receptors in adipocytes and pre-adipocytes, and it is not thought to be required for anti-diabetic efficacy. Advantageously, compounds of Formula I possess a diminished propensity towards inducing body weight gain and thus, one of the major side effects of known glitazones. Moreover, compounds of Formula I have also shown beneficial effects on plasma lipid profiles.

In one embodiment, compounds of Formula I are described in U.S. Provisional Patent Application Ser. No. 60/141,672, filed Jun. 30, 1999; WO 01/00579, published Jan. 4, 2001; to Mcgee et al., and incorporated herein by reference in their entirety for all purposes. As described therein, compounds of Formula I can be synthesized by a variety of methods, some of which are illustrated in FIG. 1. With reference to FIG. 1, using commercial available 2-chloro-5-nitrobenzonitrile (i) and treatment of (i) with a phenol, thiophenol, or optionally protected aniline in the presence of base and heat generates adduct (ii). Reduction of the nitro group in (ii) with, for example, hydrogen in the presence of Raney nickel catalyst provides an aniline derivative (iii). Sulfonylation of (iii) with an appropriate arylsulfonyl halide in the presence of base (typically a tertiary amine) provides target compound (iv). Compound (iii) can also be converted to a related compound of formula (vi) in which the orientation of the sulfonamide linkage is reversed. Thus, conversion of the aniline (iii) to the benzenesulfonyl chloride (v) can be accomplished using methods described in Hoffman, *Organic Syntheses Collective Volume VII*, p. 508-511. Subsequent treatment of (v) with an appropriate aniline provides the target compound (vi). Other compounds of the present invention can be prepared beginning with, for example, 3,4-difluoronitrobenzene, 3-chloro-4-fluoronitrobenzene, 2-chloro-5-nitroanisole, 3-bromo-4-fluoronitrobenzene and the like.

Moreover, in certain embodiments, compounds of Formula I are described in WO 99/38845, published Aug. 5, 1999, to De La Brouse-Elwood et al., and incorporated herein by reference in its entirety for all purposes. Certain compounds as described therein, are potent, selective activators of PPARγ and are useful for the treatment of NIDDM and other disorders related to lipid metabolism and energy homeostasis. In other aspects, and depending on the biological environment (e.g., cell type, pathological condition of the host, and the like.), the compounds can activate or block the actions of PPARγ. By activating the PPARγ receptor, the compounds will find use as therapeutic agents capable of modulating conditions mediated by the PPARγ receptor. Additionally, the compounds are useful for the prevention and treatment of complications of diabetes (e.g., neuropathy, retinopathy, glomerulosclerosis, and cardiovascular disorders), and treating hyperlipidemia. The compounds are useful for the modulation of inflammatory conditions which most recently have been found to be controlled by PPARγ (see, Ricote, et al., *Nature,* 391:79-82 (1998) and Jiang, et al., *Nature,* 391:82-86 (1998). Examples of inflammatory conditions include rheumatoid arthritis and atherosclerosis Compounds that act via antagonism of PPARγ are useful for treating obesity, hypertension, hyperlipidemia, hypercholesterolemia, hyperlipoproteinemia, and metabolic disorders.

Preferred compounds of Formula I are those in which $Ar^1$ is a pyridyl ring having a single substituent selected from the group consisting of halogen, —$OCF_3$ and —$CF_3$; X is a divalent linkage selected from the group of —O—, —$SO_2$—, —S—, —C(O)—, —$CH_2$— and combinations thereof; Y is a divalent linkage selected from the group of —NH—$S(O)_2$— and —NH—C(O)—; $R^1$ is selected from the group consisting of hydrogen, halogen, cyano, ($C_1$-$C_8$)alkyl, ($C_1$-$C_8$)alkoxy, —C(O)($C_1$-$C_8$ alkyl) and —C(O)$NR^{15}R^{16}$ in which $R^{15}$ and are selected from hydrogen, ($C_1$-$C_8$)alkyl, aryl and aryl($C_1$-$C_4$)alkyl; $R^2$ is a phenyl or pyridyl ring, optionally substituted by 0-3 groups selected from halogen, ($C_1$-$C_8$)alkyl, —O—($C_1$-$C_8$)alkyl, $CF_3$, and —CN; and $R^3$ is hydrogen, halogen, cyano or ($C_1$-$C_4$)alkoxy.

One of skill in the art will understand that a number of structural isomers are represented by Formula I. Preferred isomers are those in which the groups on the phenyl ring occupy positions that are not all contiguous. Particularly preferred compounds are those having the structural orientations represented by the formulae:

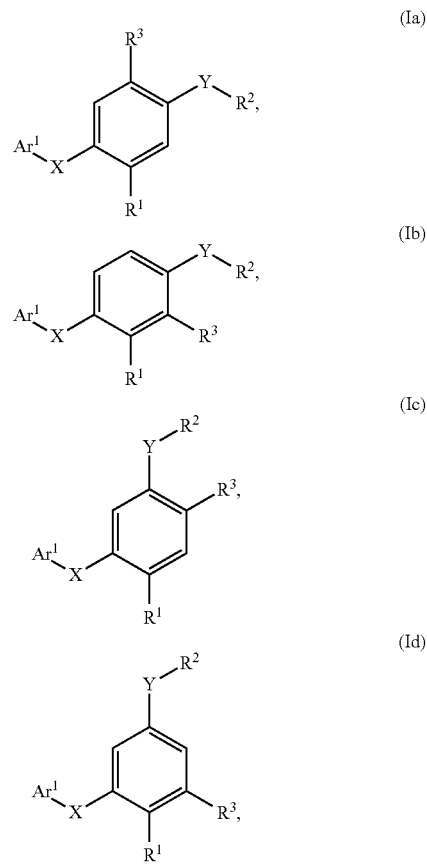

-continued

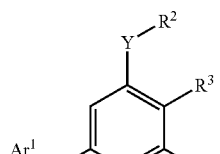
(Ie)

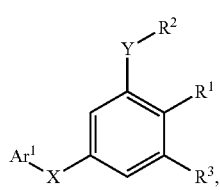
(If)

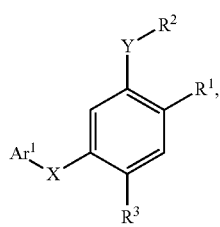
(Ig)

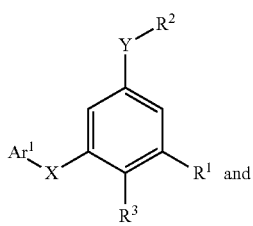
(Ih)

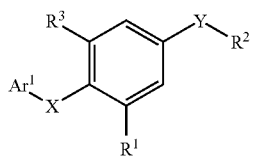
(Ii)

Still further preferred are those compounds having the structural orientation represented by formula Ia or Ib. Still other preferred compounds, are those of formula Ia or Ib in which the positions of R¹ and R³ are switched (or reversed). Yet other preferred compounds are those in which Ar¹—X— and —Y—R² occupy positions para to one another (exemplified by Ii).

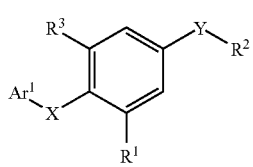
(Ii)

Still another group of preferred compounds are represented by the formula:

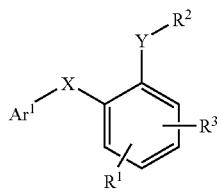
(Ij)

Equally preferred Ar¹ moieties are set forth below. Each of the rings below can be optionally substituted with one or more functional groups. In the structures below, "W" is a heteroatom such as N, O or S.

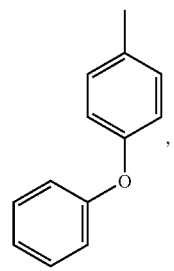
IIa

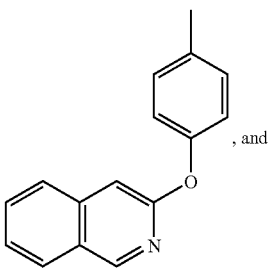
IIb

, and

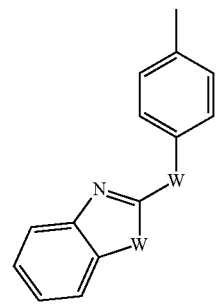
IIc

The compositions of the present invention further comprises one or more (ii) antidiabetic compounds. A wide range of antidiabetic agents can be used in the compositions and methods of the present invention. Suitable agents include, but are not limited to, one or more antidiabetic agent such as sulfonylureas, biguanides, glitazones and other PPARγ agonists, α-glucosidase inhibitors, potassium channel antagonists, aldose reductase inhibitors, glucagon antagonists, activators of RXR, insulin therapy or other anti-obesity agent, prodrugs thereof, or pharmaceutically acceptable salts of the antidiabetic agents. In certain instances, the antidiabetic agents include, but are not limited to, one or more agents such as insulin and insulin analogs (e.g. LysPro insulin); GLP-1 (7-37) (insulinotropin) and GLP-1 (7-36)-NH₂; sulfonylureas and analogs, including, but not limited to, chlorpropamide, glibenclamide, tolbutamide, tolazamide, acetohexamide, glipizide, glimepiride, repaglinide and meglitinide; biguanides, including, but not limited to, metformin, phenformin and buformin.

In another embodiment, the antidiabetic agents include various forms of insulin, such as insulin in its various dosage forms, subcutaneous, oral, inhaled, and the like, molecular variations, and short-, medium- and long-acting versions. Suitable insulin sources include, but are not limited to, recombinant human insulin, natural pig insulin, natural ox insulin, natural bovine insulin, natural human insulin, recombinant human argine-insulin, recombinant human aspartic-insulin, dalanated insulin, defalan insulin, glargine insulin, human insulin zinc, human insulin isophane, lispro insulin, neutral insulin, human proinsulin, and the like.

In one embodiment, the antidiabetic agents used in the compositions of the present invention are sulfonylureas. Preferred sulfonylureas suitable for use in the present invention include, but are not limited to, acetohexamide, chlorpropamide, glyburide, glipizide, gliclazide, glimepiride, gliquidone, glisoxepid, glibomuride, gliamilide, glibomuride, glicetanile, gliflumide, glymidine, glyparamide, tolpyrramide, glyhexamide, phenbutamide, tolazamide, tolbutamide and tolcyclamide. Those of skill in the art will know of other sulfonylureas suitable for use in the present invention.

Sulfonylureas are a group of drugs that induce hypoglycemia by stimulating insulin release from the pancreas. Generally, sulfonylureas have found wide utility in the treatment of NIDDM. Their efficacy is decreased in IDDM because of the inherent inability of the patient to produce insulin. Adverse reactions to sulfonylureas occur in a fraction of patients, particularly the elderly. One of the most severe side effects is hypoglycemia and coma. Other side effects include nausea and vomiting, cholestatic jaundice, agranulocytosis, cardiovascular mortality, aplastic and hemolytic anemias, generalized hypersensitivity reactions and dermatological reactions. The compounds of Formula I increase insulin sensitivity, and when used in combination with sulfonylureas, increase the efficacy and side effect profile of either type of agent alone. In certain instances, the combination therapy allows the use of lower doses of both agents.

In certain embodiments, the sulfonylurea used in the compositions of the present invention have the following formula:

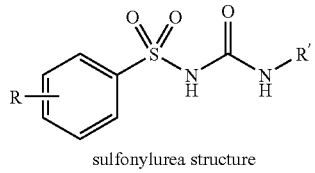

sulfonylurea structure

II wherein R is H, halogen, alkyl, alkanoyl, aryl, arylalkyl, heteroaryl, aroylaminoalkyl, heteroaroylaminoalkyl, or cycloalkyl; and R' is alkyl, cycloalkyl and heterocycloalkyl (including those that are listed to the rest of the molecule via a heteroatom that is part of R'). Preferred sulfonylureas are those in which R is 4-chloro, 4-methyl, 4-acetyl, 4-[2-[(3-chloro-5-methoxybenzoyl)amino]ethyl] or 4-[2-[(5-methyl-2-pyrazinylcarbonyl)amino]ethyl]; and R' is propyl, butyl, 1-piperidyl, cyclohexyl, cycloheptyl, 4-dimethylaminophenyl, 1-hexahydroazepine, or 3-azabicyclo[3.3.0]oct-3-yl.

In another embodiment, the antidiabetic agents used in the compositions of the present invention are biguanides. Biguanides are a group of drugs that are efficacious in the treatment of hyperglycemia. Preferred biguanides suitable for use in the present invention include, but are not limited to, metformin, phenformin and buformin. Unlike the sulfonylureas, metformin does not induce release of insulin from the pancreas. Without being bound by any particular theory, it is thought that its effects are mediated by increasing insulin activity in peripheral tissues, reducing hepatic glucose output due to inhibition of gluconeogenesis and reducing the absorption of glucose from the intestine. Side effects associated with the use of biguanides include lactic acidosis, diarrhea, nausea, and anorexia.

In certain aspects, the biguanides used in the compositions of the present invention have the following formula:

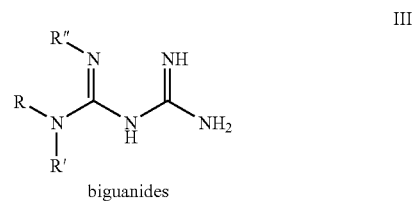

biguanides

III wherein R, R' and R" are each selected independently from H, alkyl, cycloalkyl, aryl, arylalkyl heteroalkyl, heteroaryl, heteroarylalkyl and aryl-heteroalkyl. Preferably, R, R' and R" are each independently selected from hydrogen, $(C_1-C_3)$alkyl and aryl-$(C_1-C_3)$ alkyl. Preferred biguanides include metformin, buformin, etoformin and phenformin.

In another embodiment, the antidiabetic agent is a glitazone. Glitazones, also known as thiazolidinediones, produce antidiabetic effects by modulating the activity of the nuclear receptor PPARγ. Particularly preferred members of this group of antidiabetic agents have the following formula:

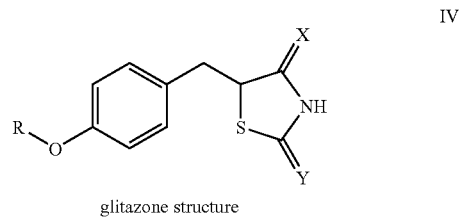

glitazone structure

Figure 2:
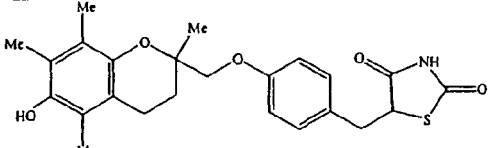
FIG. 2 shows illustrative antidiabetic agents.
Figure 2:
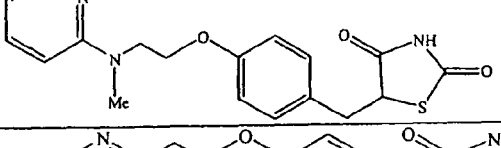
Figure 2:
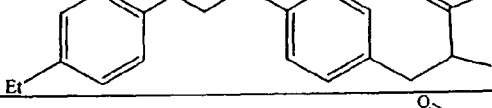
Figure 2:
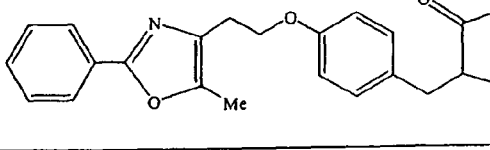
Figure 2:
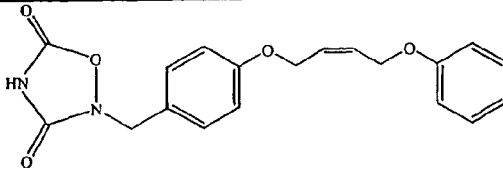
Figure 2:
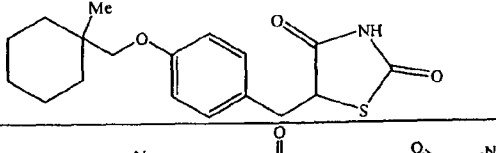
Figure 2:
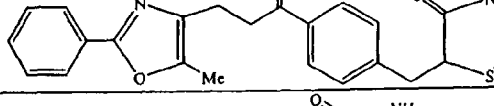
Figure 2:
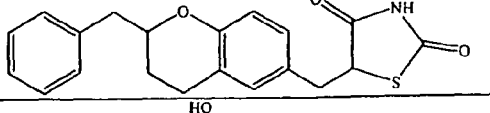
Figure 2:
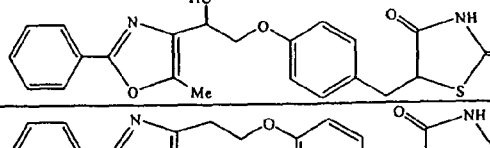
Figure 2:
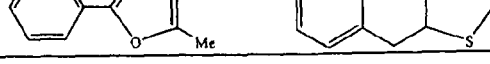

IV wherein R is a functional group containing from six to twenty carbon atoms and at least one aromatic or non-aromatic ring system; and X and Y are each selected independently from O, S or NH. Suitable glitazone compounds are disclosed in *Current Pharmaceutical Design,* 1996; 2:85-101, incorporated herein by reference, and include compounds such as troglitazone, rosiglitazone, pioglitazone, JTT-0.501, YM-440, ciglitazone, darglitazone, englitazone, AD-5075, and BM-131246. Preferably, the glitazone compounds used in the present invention include troglitazone, rosiglitazone, and pioglitazone. Other PPARγ activators that are not part of the glitazone family, such as GW-409544 and GI-262570, can be used. FIG. 2 sets forth PPARγ modulators suitable for use in the present invention.

In certain aspects, PPARγ modulators are disclosed in WO 99/58510, published Nov. 18, 1999, to Momose et al., and incorporated herein by reference in its entirety for all purposes. As disclosed therein, oxyiminoalkanoic acid derivatives are disclosed that are useful for treating and/or preventing diabetes mellitus, hyperlipemia, impaired glucose tolerance, inflammatory disease and arteriosclerosis. Moreover, the compounds are useful for controlling retinoid-related receptors, enhancing insulin sensitivity and improving insulin resistance, and for treating and preventing diabetic complications. Other PPARγ modulators are disclosed in WO 99/38850, published Aug. 5, 1999, to Lohray et al., and incorporated herein by reference in its entirety for all purposes.

In another embodiment, the present invention provides compositions comprising compounds of Formula I and α-glucosidase inhibitors. Preferred α-glucosidase inhibitors include acarbose, celgosivir, camiglibase, voglibose and miglitol. Suitable α-glucosidase inhibitors are disclosed in WO 99/29327, to Odaka et al., published Jun. 17, 1999, entitled "Use of an α-glucosidase inhibitor to treat high-risk impaired glucose tolerance" and incorporated herein by reference in its entirety for all purposes. As described therein, the α-glucosidase inhibitor is particularly useful in the treatment of non-insulin-dependent diabetes mellitus. In addition, WO 99/26606, published Jun. 3, 1999, to Goldman et al., and entitled "Sustained-release formulations of α-glucosidase inhibitors," and incorporated herein by reference in its entirety for all purposes, discloses sustained released formulations of α-glucosidase inhibitors, e.g. acarbose useful in the present invention.

Other types of agents that have found limited utility in treating diabetes include potassium channel antagonists such as repaglinide, and aldose reductase inhibitors such as zopolrestat, minalrestat, ponalrestat and tolrestat. Still in the experimental stage, glucagon antagonists, activators of the retinoid-X receptor (RXR), and anti-obesity agents are also being evaluated as potential antidiabetic agents. Others agents suitable for use in the present invention include, but are not limited to, glucagon, and miscellaneous agents such as methyl palmoxirate, palmoxirate sodium, pirogliride, pramlintide, amlintide, seglifide.

Methods, Uses, Dosages and Schedules

In another embodiment, the present invention provides a method for modulating conditions associated with diabetes or diabetes-related disorders in a host, comprising administering to the host an efficacious amount of compositions comprising (i) a compound of Formula I in combination with (ii) one or more antidiabetic agents. In certain aspects, the compositions of the present invention that are administered comprise a compound of Formula I formulated together with one or more antidiabetic agents. Alternatively, the composition that is administered comprises a compound of Formula I independently formulated from one or more antidiabetic agents i.e., separately formulated.

The pharmaceutical compositions of the present invention are suitable for use in a variety of drug delivery systems. Examples of suitable formulations for use in the present invention are found in *Remington's Pharmaceutical Sciences* (Mack Publishing Company, Philadelphia, Pa., 17th ed. (1985)), which is incorporated herein by reference. In addition, for a brief review of methods for drug delivery, see, Langer, *Science* 249:1527-1533 (1990), which is incorporated herein by reference.

The pharmaceutical compositions of the present invention are intended for parenteral, topical, oral or local administration. In certain aspects, the pharmaceutical compositions are administered parenterally, e.g., intravenously, subcutaneously, intradermally, or intramuscularly. In one embodiment, the invention provides compositions for parenteral administration which comprise a compound of Formula I, an antidiabetic agent as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well-known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid formulations, compounds of Formula I can be admixed with conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the compounds of Formula I and antidiabetic agents are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of Formula I or a pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

In powders, the carrier is a finely divided solid that is in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

In therapeutic use for the treatment of obesity, NIDDM, or inflammatory conditions, the compounds utilized in the pharmaceutical method of the invention are administered at the initial dosage of about 0.001 mg/kg to about 100 mg/kg daily. A daily dose range of about 0.1 mg/kg to about 10 mg/kg is preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages that are less than the optimum dose of the compound. Thereafter, the dosage is increased by small increments until the optimum effect under circumstances is reached. For convenience, the total daily dosage may be divided and administered in portions during the day, if desired.

In therapeutic applications, the compounds of Formula I and antidiabetic agents of the present invention are administered to a patient in a combination amount sufficient to elicit a response. An amount adequate to accomplish this is defined as "therapeutically effective combination dose." The methods include the administration of the combination of compound of Formula I with antidiabetic agent wherein the two components are delivered in a simultaneous manner, in combination therapy wherein the compound of Formula I is administered first, followed by the antidiabetic agent, as well as wherein the antidiabetic agent is delivered first followed by the compound of Formula I.

Since the present invention has an aspect that relates to a combination of active ingredients which can be administered separately, the invention also relates to combining separate pharmaceutical compositions in kit form. The kit comprises two separate pharmaceutical compositions: a compound of Formula I, a prodrug thereof or a pharmaceutically acceptable salt and a second compound such as an antidiabetic agent as described above. The kit comprises a container for containing the separate components such as a divided bottle or a divided foil packet, however, the separate components can also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Effective combination amounts for various uses will depend on, for example, the particular antidiabetic agent, the compound of Formula I employed, the manner of administration, the weight and general state of health of the patient, and the judgment of the prescribing physician. In one embodiment, composition or formulation to be administered will contain a quantity of a compound(s) according to Formula I in an amount effective to treat the disease/condition of the subject being treated, e.g., a glycogen phosphorylase dependent disease/condition. The amount of antidiabetic agent will depend in part to the chemical class.

In certain instances, administration of the compounds of Formula I can be via any method which provides systemic exposure to the compound of this invention, preferably to the muscle and fatty tissue. These methods include oral routes, parenteral, intraduodenal routes, etc. Generally, the compounds of the present invention are administered in single (e.g., once daily) or multiple doses. The compounds of the present invention are generally administered in the form of a pharmaceutical composition comprising at least one of the compounds of Formula I together with a pharmaceutically acceptable carrier or diluent. Thus, the compounds of this invention can be administered individually or together in any conventional oral, parenteral or transdermal dosage form.

For oral administration, a pharmaceutical composition can take the form of solutions, suspensions, tablets, pills, capsules, powders, and the like. Tablets containing various excipients such as sodium citrate, calcium carbonate and calcium phosphate are employed along with various binders such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

It will be appreciated that the actual preferred course of therapy will vary according to, inter alia, the mode of administration of the compound of Formula I, the particular formulation of the antidiabetic agent being utilized, the mode of administration of the compounds, the particular disease being treated and the particular host being treated. The optimal course of therapy for a given set of conditions can be ascertained by those skilled in the art using conventional course of therapy determination tests and in view of the information set out herein.

Additional Uses for Compounds of Formula I

The compounds of Formula I have been recently shown to interact with PPARγ from human and other species. Some of the compounds of Formula I show various degrees of intrinsic activity towards PPARγ; that is, some of them display significant PPARγ activation, while others possess a distinct PPARγ antagonist-like profile. As such, specific compounds of Formula I are well suited for the treatment of the various conditions and diseases recently established to be mediated by, or linked to PPARγ activity levels. Tables I, II, and III below outline other indications in which the compositions of the present invention are useful.

TABLE I

Metabolic Conditions

1. Diabetes and Conditions Secondary to Diabetes
    Hypertension
    Angina pectoris
    Dyslipidemia
        Hypertriglyceridemia
        Hyperlipoproteinemias
        Hypercholesterolemia
    Gout
    Nephropathy and other renal diseases secondary to diabetes
    Diabetic neuropathy.
2. Other insulin-resistance-related diseases
Polycystic ovarian syndrome,
Glucocorticoid-induced insulin resistance
3. Obesity
PPARγ agonists promote adipocyte differentiation and fat accumulation. PPARγ antagonists block normal hormone-mediated differentiation of preadipocytes into adipocytes. (See, Wright et al., J. Biol. Chem. 275(3) 1873-1877 (2000).)
PPARγ agonists inhibit expression of ob gene (leptin production) in mature adipocytes. It follows that PPARγ antagonists will increase leptin production with ensuing decrease in appetite and food consumption. (See, Sinha et al., Metab. Clin. Exp., 48 (6) 786-791 (1999).)
Hyperleptinemia condition (which can be induced with a PPARγ antagonist) in rats results in downregulation of PPARγ expression and upregulation of fatty acid-oxidizing enzymes. Also accompanied by a reversal of adipocyte differentiation. Suggests that relatively short-term treatment with high dose of PPARγ antagonist will have long-lasting effects on obesity (conventional treatments of obesity reduce fat content in mature adipocytes but leaves them with lipogenic enzymes capable of rapid resynthesis of fat, likely to be responsible for treatment failure). (See, Zhou et al., Proc. Natl. Acad. Sci. USA 96 (5) 2391-2395 (1999).)
PPARγ agonists upregulate UCP2 expression in adipocytes and skeletal muscle, resulting in increased energy expenditure. (See, Viguerie-Bascands et al., Biochem. Biophys. Res. Commun. 256 (1) 138-141 (1999) and Camirand et al., Endocrinology 139 (1) 428-431 (1998).)
PPARγ is critical for controlling expression of UCP2 and UCP3 in adipose tissue. (See, Kelly et al., Endocrinology 139 (12) 4920-4927 (1998).)
4. Hypertension
PPARγ agonists suppress endothelin-1 secretion by vascular endothelial cells and result in decreased blood pressure. (See, Satoh et al., Biochem. Biophys. Res. Commun. 254 (3) 757-763 (1999) and Itoh et al., Clin. Exp. Pharmacol. Physiol. 26 (7) 558-560 (1999).)
PPARγ agonists decrease blood pressure in various models of hypertension. (See, Komers et al., Physiol. Res. (Prague) 47 (4) 215-225 (1998).)
5. Lipid Disorders
PPARγ has been implicated in systemic glucose and lipid homeostasis. (See, Kliewer et al., xCurr. Opin. Genet. Dev. 8 (5) 576-581 (1998).)
PPARγ agonists improve hypertriglyceridemia. (See, Berger et al., J. Biol. Chem. 274 (10) 6718-6725 (1999).)
PPARγ agonists are antihyperlipidemic. (See, Henke et al., J. Med. Chem. 41 (25) 5020-5036 (1998).)
PPARγ activator shown to increase high-density lipoprotein (HDL) in dose-dependent manner. Also decreased VLDL, LDL and triglycerides. (See, Bisgaier et al., J. Lipid Res. 39 (1) 17-30 (1998).)
6. Atherosclerosis
Activated monocytes/macrophages express PPARγ and PPARγ activation downregulates the induced macrophage production of IL-1 and TNFα. Potential implications for atherosclerosis. (See, McCarty et al., J. Med. Food 1 (3) 217-226 (1999).)
PPARγ mediates the effects of non-esterified fatty acids (NEFA) on smooth muscle cells, which alter the extracellular matrix in the intima of small and large arteries. These changes can lead to increased deposition of LDL and may be associated with the etiology of atherosclerosis. Modulators of PPARγ will affect this process. (See, Olsson et al., Diabetes 48 (3) 616-622 (1999).)

TABLE I-continued

Metabolic Conditions

PPARγ agonists inhibit proliferation, hypertrophy andmigration of vascular smooth muscle cells induced by growth factors. These processes are crucial in the development of vascular remodeling, atherosclerosis.
PPARγ involved in negative regulation of monocyte/macrophage function in atherosclerotic plaques and regulates expression of matrix metalloprotease-9, an enzyme implicated in plaque rupture. In this case, a PPARγ agonist may be useful. (See, Marx et al., Am. J. Pathol. 153 (1) 17-23 (1998) and Shu et al., Biochem. Biophys. Res. Commun. 267 (1) 345-349 (2000).)
PPARγ is expressed in macrophage foam cells of human sclerotic lesions. (See, Ricote et al., Proc. Natl. Acad. Sci. USA 95 (13) 7614-7619 (1998).)
PPARγ is expressed in atherosclerotic plaques and in endothelial cells. In endothelial cells, PPARγ agonists markedly attenuate the TNFα-induced expression of VCAM-1 and ICAM-1 (vascular cell adhesion molecules) in vitro. PPARγ agonists significantly reduce monocyte/macrophage homing to atherosclerotic plaques in apoE-deficient mice. These effects combined may have beneficial effects in modulating inflammatory response in atherosclerosis. (See, Pasceri et al., Circulation 101 (3) 235-238 (2000).)
Human genetic evidence also suggests that PPARγ plays significant role in atherogenesis, independently from effects on obesity and lipid metabolism, possibly via a direct local vascular wall effect. (See, Wang et al., Cardiovasc. Res. 44 (3) 588-594 (1999).)
In the past year, there has been a very significant increase in research implicating PPARγ in macrophage biology, cell cycle regulation and atherosclerosis. PPARγ as regulator of monocyte/macrophage function. (See, Ricote et al., J. Leukocyte Biol. 66 (5) 733-739 (1999).)
7. Bone Disorders
TZDs inhibit in vitro bone nodule formation and mineralization. (See, Johnson et al., Endocrinology 140 (7) 3245-3254 (1999).)
PPARγ polymorphism affects bone mineral density in postmenopausal women. (See, Ogawa et al., Biochem. Biophys. Res. Commun. 260 (1) 122-126 (1999).)
TZDs are potent inhibitors of bone resorption in vitro. Thus, TZDs may suppress bone resorption in diabetic patients and prevent bone loss. (See, Okazaki et al., Endocrinology 140 (11) 5060-5065 (1999).)
Short-term treatment of diabetic patients with TZD decreases bone turnover. This effect is noted before significantly improvement on glucose metabolism, suggesting that effect is direct on bone. Dual effects on glucose and bone metabolism may lead to spared bone mass in diabetic patients. (See, Okazaki et al., Endocr. J. (Tokyo) 46 (6) 795-801 (1999).)
8. Female - Specific Conditions
PPARγ agonists can be used to inhibit excessive uterine bleeding in women (climacteric). (See, Urban et al., WO-9839006.)
9. Acne
PPARγ implicated in the differentiation of sebocytes. PPARγ agonists may be used in the treatment of acne. (See, Rosenfield et al., Dermatology (Basel) 196 (1) 43-46 (1998).)
Other skin disorders associated with differentiation of epidermal cells. (See, Rivier et al., FR 2773075-A1.)
Proliferative diseases of the skin. (See, Pershadsingh et al., U.S. Pat. No. 5,981,586.)
10. Cell Proliferation
In combination with a retinoid-X receptor agonist, a PPARγ agonist reduces uncontrolled cell proliferation, including cancer, restenosis and atherosclerosis. PPARγ agonists, alone or in combination with known agents, may reduce proliferative response seen following angioplasty, vessel transplant or endarectomy.

TABLE 2

CNS

1. Alzheimer's
PPARγ agonists inhibit b-amyloid stimulated secretion of proinflammatory products by microglia and monocytes that are responsible for neurotoxicity and astrocyte activation. They also arrest differentiation of monocytes into activated macrophages, and inhibit b-amyloid-stimulated expression of IL-6, TNFα and cyclooxigenase-2. (See, Combs et al., J. Neuroscience 20 (2) 558-567 (2000).)
In temporal cortex from AD patients, cyclooxygenase-1 and -2 levels were increased. PPARγ levels were also increased. Certain agents that activate PPARγ inhibit COX-2 expression in glial cells. (See, Kitamura et al., Biochem. Biophys. Res. Commun. 254 (3) 582-586 (1999).)
PPARγ agonists protect cerebellar granule cells from cytokine-induced apoptotic death by inhibition of iNOS. (See, Heneka et al., J. Neuroimmunol. 100 (1-2) 156-168 (1999).)
Activated monocytes/macrophages express PPARγ and PPARγ activation downregulates the induced macrophage production of IL-1 and TNFα. Potential implications for AD. (See, McCarty et al., J. Med. Food 1 (3) 217-226 (1999).)

TABLE 2-continued

| CNS |
|---|

2. Neuroinflammation
PPARγ agonists inhibit LPS and IFN-g induced expression of iNOS by glial cells. (See, Kitamura et al., Neurosci. Lett. 262 (2) 129-132 (1999).)
PPARγ ligands may also be relevant for other disorders associated with neuroinflammation, such as ischemic stroke, closed-head injury, and multiple sclerosis.

TABLE 3

| Chemotherapy |
|---|

1. Cancer
Antiangiogenic affect of PPARγ agonists are mediated by apoptotic stimulus on endothelial cells. (See, Bishop-Balley et al., J. Biol. Chem. 274 (24) 17042-17048 (1999).)
PPARγ agonists induce terminal differentiation and growth arrest of human colon cancer cells. (See, Kitamura et al., Jpn. J. Cancer Res. 90 (1) 75-80 (1999) and Sarraf et al., Nat. Med. (NY) 4 (9) 1046-1052 (1998).)
PPARγ agonists enhance the antiproliferative effects of retinoic acid on human colon cancer cells. (See, Brockman et al., Gastroenterology 115 (5) 1049-1055 (1998).)
PPARγ agonist has potent antitumor effect against human prostate cancer in vitro and in vivo. (See, Kubota et al., Cancer Res. 58 (15) 3344-3352 (1998).)
PPARγ agonists cause inhibition of proliferation of cultured human breast tumor cells and induces apoptosis. Effects also seen in vivo (mice). (See, Elstner et al., Proc. Natl. Acad. Sci. USA 95 (15) 8806-8811 (1998).)
PPARγ agonists induce terminal differentiation of malignant breast epithelial cells. (See, Mueller et al., Mol. Cell 1 (3) 465-470 (1998) and Yee et al., Int. J. Oncol. 15 (5) 967-973 (1999).)
PPARγ agonists are useful in the treatment of liposarcomas. (See, Evans et al., WO-9829120.)
PPARγ highly expressed in all human transitional epithelial cell cancers, including uroepithelial human cancers. PPARγ agonists induce differentiation and inhibit proliferation. (See, Guan et al., Neoplasia (NY) 1 (4) 330-339 (1999).)
Differentiation of many cell types (hepatocytes, fibroblasts, adipocytes, keratinocytes, myocytes, and monocyte/macrophages) involves PPARγ. PPARγ modulators may play role in treating malignancies that result from these and other cell types. (See, Varmecq et al., Lancet 354 (9173) 141-148 (1999).)

TABLE 4

| Inflammation/Immune |
|---|

1. Inflammation/Immune
PPARγ is markedly upregulated in activated macrophages. PPARγ involved in negative regulation of monocyte/macrophage function, including generation of inflammatory cytokines, expression of iNOS, gelatinase B and scavenger receptor A. PPARγ agonists may be of value. (See, Marx et al., Am. J. Pathol. 153 (1) 17-23 (1998).)
Incremental therapeutic benefit of NSAIDs (some of which activate PPARγ) in the treatment of rheumatoid arthritis may be mediated via PPARγ activation. (See, Jiang et al., Nature 391 (6662) 82-86 (1998).)
PPARγ agonists inhibit iNOS production by activated macrophages. PPARγ agonists may be useful. (See, Colville-Nash et al., J. Immunol. 161 (2) 978-984 (1998).)
PPARγ agonists attenuate antigen-induced cytokine production by bone-marrow-derived mast cells. (See, Sugiyama et al., FEBS Lett. 467 (2-3) 259-262 (2000).)
Recently, an immunomodulatory role for PPARγ has been described in cells critical to the innate immune system, the monocyte/macrophage. PPARγ agonists have been shown to mediate significant inhibition of proliferative responses of helper T-cell clones and freshly isolated splenocytes. Thus, IL-2 production by the T-cell clones is inhibited by PPARγ agonists, which may have utility as immunosuppressants. (See, Clark et al., J. Immunol. 164 (3) 1364-1371 (2000).)
PPARγ as regulator of monocyte/macrophage function. (See, Ricote et al., J. Leukocyte Biol. 66 (5) 733-739 (1999).)
PPARγ expression in WBC may play a role in host response to acute inflammatory challenge and may prove to be an important target for anti-inflammatory control. (See, Leininger et al., Biochem. Biophys. Res. Gommun. 263 (3) 749-753 (1999).)
PPARγ activators may help limit chronic inflammation mediated by vascular cell adhesion molecule VCAM-1 and monocytes. (See, Jackson et al., Arterioscler., Thromb., Vasc. Biol. 19 (9) 2094-2104 (1999).)
PPARγ agonists significantly attenuate cytokine production in colon cell lines by inhibiting activation of the nuclear factor NF-kB. PPARγ agonists also markedly reduce colonic inflammation in a mouse model of inflammatory bowel disease (IBD). PPARγ agonists may be useful in treating colitis and Crohn's disease (human forms of IBD). (See, Su et al., J. Clin. Invest. 104 (4) 383-389 (1999).)

TABLE 4-continued

Inflammation/Immune

2. Ophthalmic
Macular Degeneration
Antiangiogenic affect of PPARγ agonists mediated by apoptotic stimulus on endothelial
cells. (See, Bishop-Balley et al., J. Biol. Chem. (1999) 274 (24) 17042-17048.)
3. Antiangiogenic The invention will be described in greater detail by way of specific examples. The following examples are offered for illustrative purposes, and are not intended to limit the invention in any manner.

EXAMPLES

Example 1

This example sets forth a synthesis procedure used to generate compounds of Formula I. Compounds of Formula I were synthesized using methods as outlined in FIG. 1.

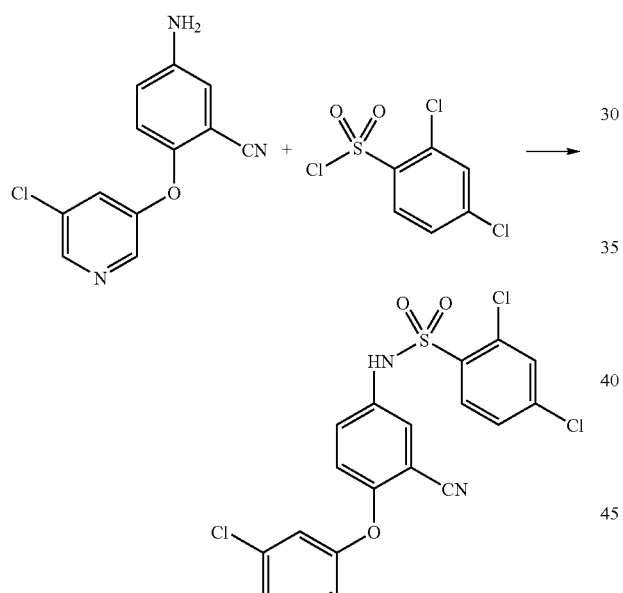

To a mixture of 5-amino-2-(3-chloro-5-pyridyloxy)benzonitrile (0.457 g) in methylene chloride was added 2,4-dichlorobenzenesulfonyl chloride (0.456 g, from Maybridge), followed by pyridine (150 μL). The reaction progress was monitored by TLC, and upon completion the solvent was removed under vacuum. The resulting residue was partitioned between methylene chloride and water. The organic layer was drawn off and concentrated. The residue was triturated with ether to provide 0.447 g of the title compound as a white solid, mp 154-156° C.

$^1$H NMR (400 MHz) (CDCl$_3$) δ 8.59 (s, 1H); 8.42 (s, 1H) 8.08 (d, J=8.5 Hz, 1H); 7.72 (t, J=1.8, 1H); 7.605 (d, J=2.7 Hz, 1H) 7.53 (dd, J=8.5, 2 Hz, 1H); 7.48 (dd, J=9.4 Hz, 1H); 7.22 (s, 1H); 7.0 (d, J=9.0 Hz, 1H). m/e (M−H) 456.

The product from above was oxidized to the corresponding pyridine N-oxide using 3-chloroperoxybenzoic acid in methylene chloride to provide the product as a white solid. m/e 470 (M+H).

Using a similar method and protocol, the following compounds were generated.

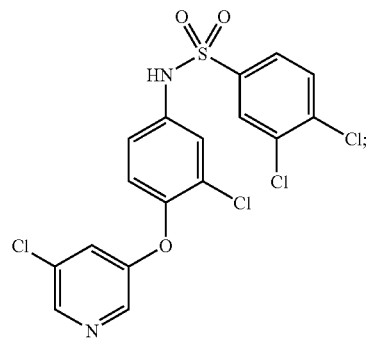

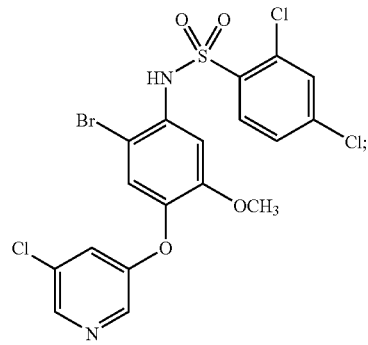

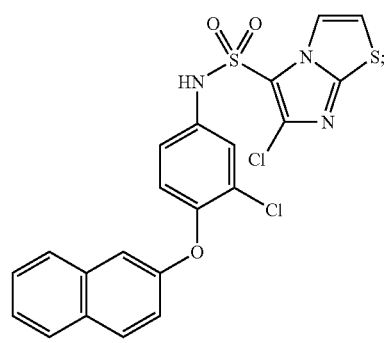

-continued

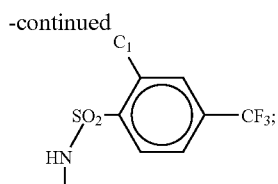

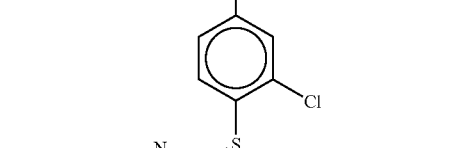

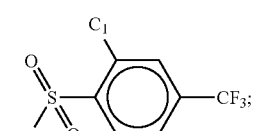

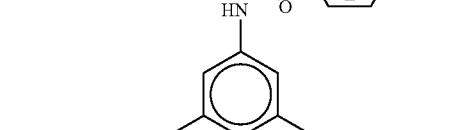

Figure 3:
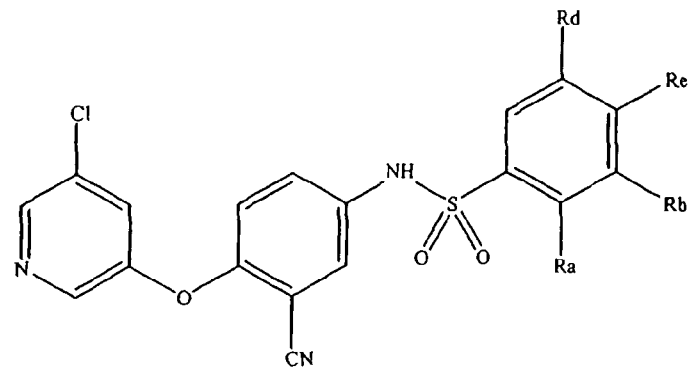
FIG. 3 illustrates various compounds of Formula I.
Figure 3:
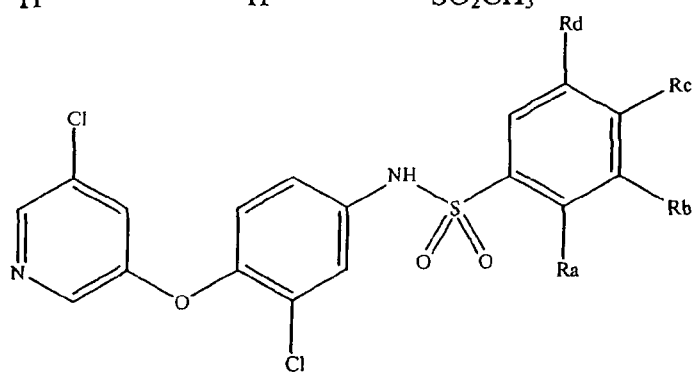
Figure 3:
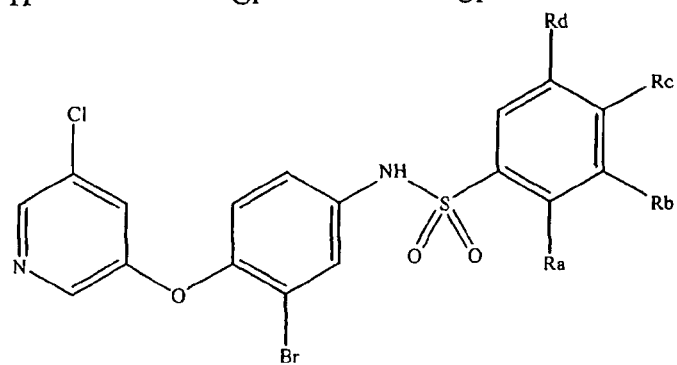
Figure 3:
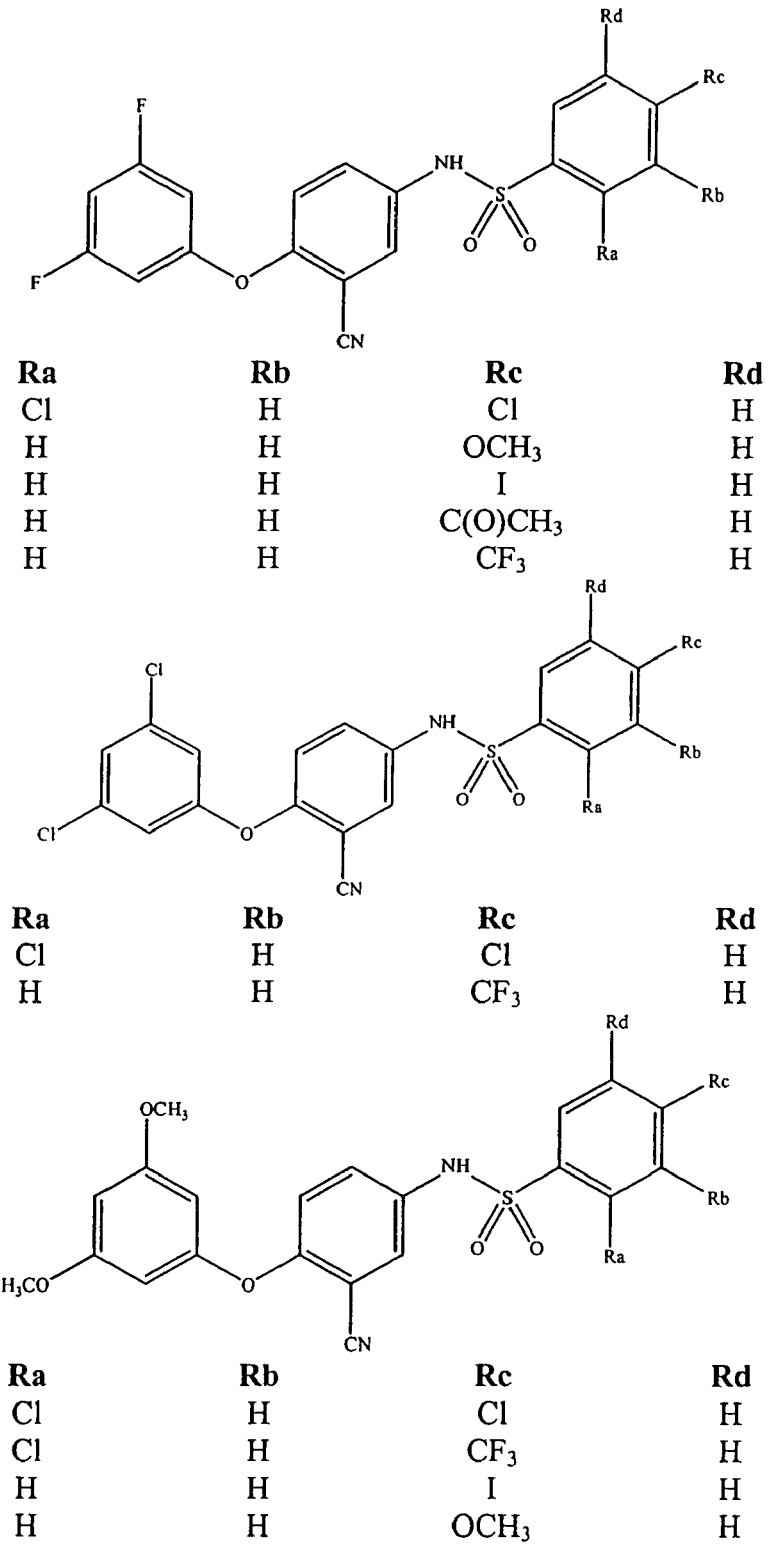
Figure 3:
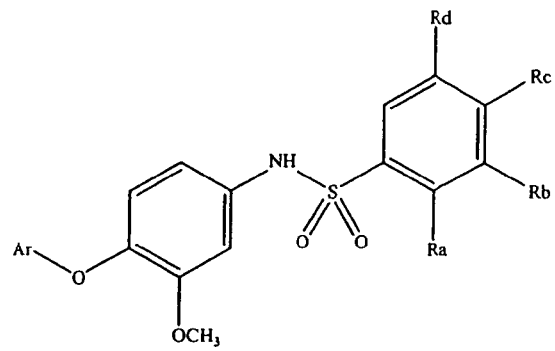
Figure 3:
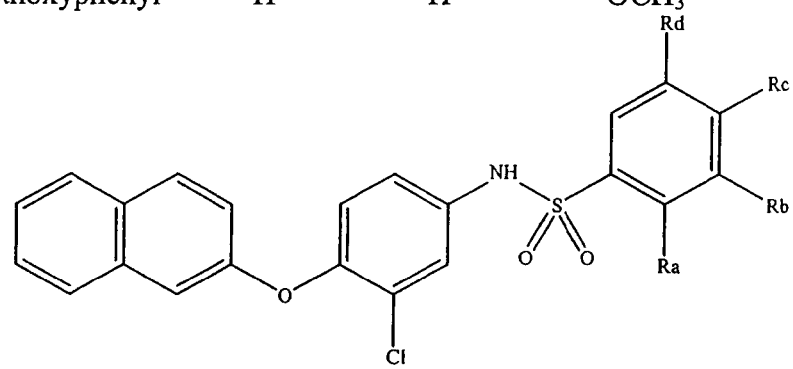
Figure 3:
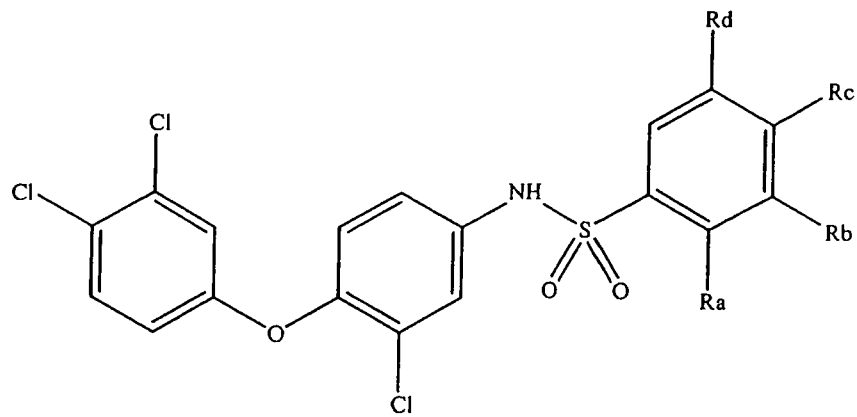
Figure 3:
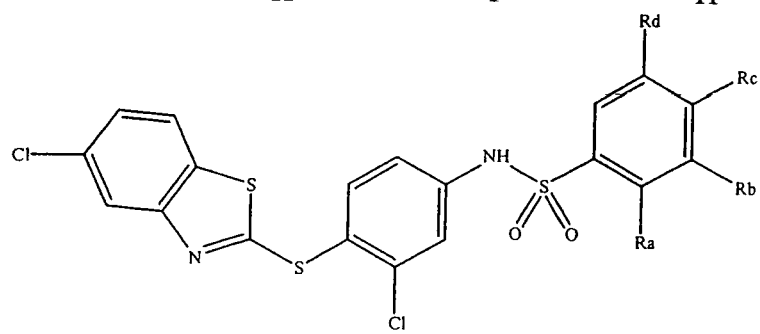
Figure 3:
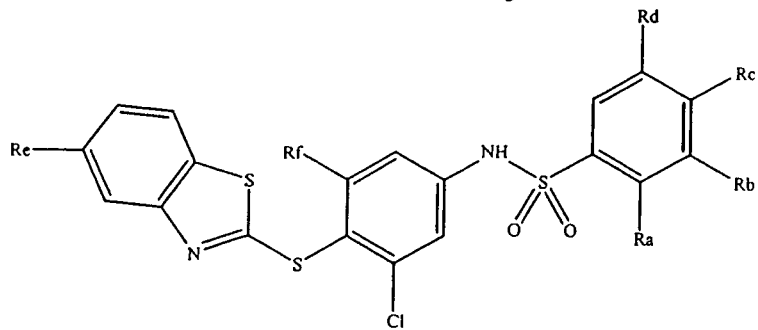
Figure 3:
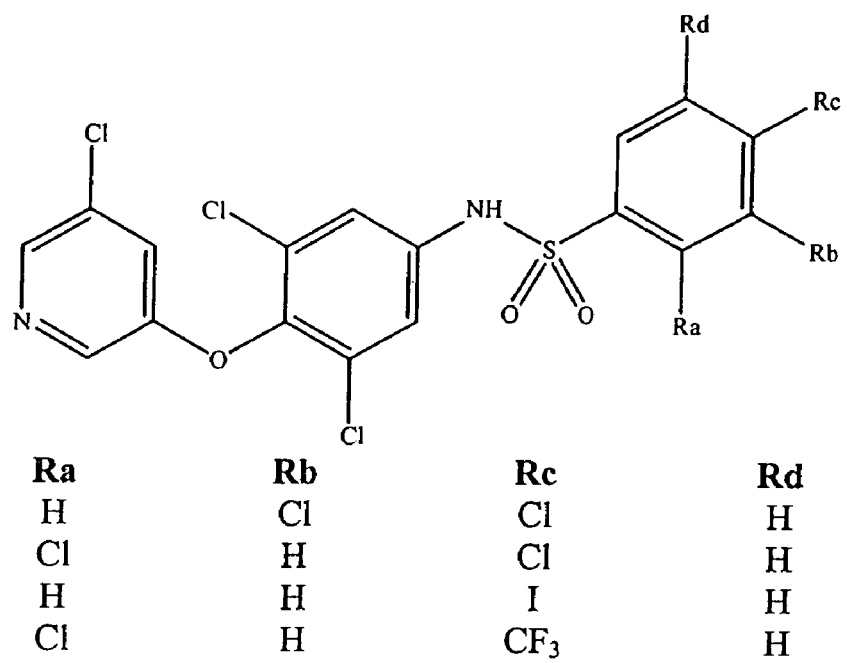

Various other compounds of Formula I are illustrated in FIG. 3.

Example 2

This example illustrates combination therapy of a compound of Formula I and a glitazone by oral administration.

Patients having NIDDM (Type II diabetes mellitus) are selected for therapy. The patients weigh between 70-100 kilograms. A compound of Formula I is orally administered in a dosage of 20 to 1,000 milligrams twice daily, more typically 100 mg twice daily. For infants or children the doses suggested are lowered in a linear fashion based on body weight or surface area.

Half the patient population is administered troglitazone as well as a compound of Formula I using an effective dose of both agents. The other half of the patients are administered an effective dose of troglitazone. The patients are monitored for improvement in the manifestations of the disease and for side effects, such as body weight gain and signs of liver toxicity.

The results indicate the administration of a combination of i) a compound of Formula I with ii) troglitazone increases the efficacy of either agent alone. The composition also provides concomitant decrease in the side effects of either agent alone.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A pharmaceutical composition, said composition comprising:
i) a compound having the formula (I) or a pharmaceutically acceptable salt thereof:

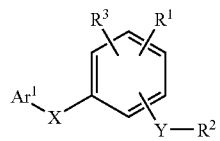

wherein $Ar^1$ is a substituted or unsubstituted phenyl, naphthyl, benzothiazole, benzimidazole, or isoquinoline group;

X is a divalent linkage selected from the group consisting of $(C_1-C_6)$alkylene, $(C_1-C_6)$alkylenoxy, $(C_1-C_6)$alkylenamino, $(C_1-C_6)$alkylene-$S(O)_k$—, —O—, —C(O)—, —N($R^{11}$)—, —N($R^{11}$)C(O)— and —S(O)$_k$—, wherein $R^{11}$ is a member selected from the group consisting of hydrogen, $(C_1-C_8)$alkyl, $(C_1-C_8)$heteroalkyl and aryl$(C_1-C_4)$alkyl; and the subscript k is an integer of from 0 to 2;

Y is a divalent linkage selected from the group consisting of alkylene, —O—, —C(O)—, —N($R^{12}$)—S(O)$_m$—, —N($R^{12}$)—S(O)$_m$—N($R^{13}$)—, —N($R^{12}$)C(O)— and —S(O)$_n$—;

wherein $R^{12}$ and $R^{13}$ are members independently selected from the group consisting of hydrogen, $(C_1-C_8)$alkyl, $(C_1-C_8)$heteroalkyl and aryl$(C_1-C_4)$alkyl; and the subscripts m and n are independently integers of from 0 to 2;

$R^1$ is a member selected from the group consisting of hydrogen, heteroalkyl, arylalkyl, halogen, cyano, nitro, $(C_1-C_8)$alkyl, $(C_1-C_8)$alkoxy, —C(O)$R^{14}$, —CO$_2R^{14}$, —C(O)NR$^{15}R^{16}$, —S(O)$_p$—R$^{14}$, —S(O)$_q$, —NR$^{15}R^{16}$, —O—C(O)—OR$^{17}$, —O—C(O)—R$^{17}$, —O—C(O)—NR$^{15}$NR$^{16}$, —N(R$^{14}$)—C(O)—NR$^{15}R^{16}$, —N(R$^{14}$)—C(O)—R$^{17}$ and —N(R$^{14}$)—C(O)—OR$^{17}$;

wherein $R^{14}$ is a member selected from the group consisting of hydrogen, $(C_1-C_8)$alkyl, $(C_1-C_8)$heteroalkyl, aryl and aryl$(C_1-C_4)$alkyl;

$R^{15}$ and $R^{16}$ are members independently selected from the group consisting of hydrogen, $(C_1-C_8)$alkyl, $(C_1-C_8)$ heteroalkyl, aryl and aryl($C_1$-$C_4$)alkyl, or taken together with the nitrogen to which each is attached form a 5-, 6- or 7-membered ring;

$R^{17}$ is a member selected from the group consisting of alkyl, heteroalkyl, aryl and arylalkyl;

the subscript p is an integer of from 0 to 3; and the subscript q is an integer of from 1 to 2; and $R^2$ is a member selected from the group consisting of ($C_1$-$C_8$)alkyl, ($C_1$-$C_8$)heteroalkyl, aryl and aryl($C_1$-$C_4$)alkyl; and $R^3$ is a member selected from the group consisting of halogen, cyano, nitro, ($C_1$-$C_8$)alkyl and ($C_1$-$C_8$)alkoxy; and ii) one or more antidiabetic agents, or pharmaceutically acceptable salts of said one or more antidiabetic agents; wherein said antidiabetic agent is a member selected from the group consisting of a sulfonylurea, an α-glucosidase inhibitor, a potassium channel antagonist, an aldose reductase inhibitor, insulin and insulin analogs, and mixtures thereof; wherein the sulfonylurea is a member selected from the group consisting of acetohexamide, chlorpropamide, glyburide, glipizide, gliclazide, glimepiride, gliquidone, glisoxepid, glibornuride, gliamilide, glicetanile, gliflumide, glymidine, glyparamide, tolpyrramide, glyhexamide, phenbutamide, tolazamide, tolbutamide and tolcyclamide;

the α-glucosidase inhibitor is a member selected from the group consisting of acarbose, miglitol, emiglitate, voglibose, MDL-25,637, camiglibose and MDL-73,945;

the potassium channel antagonist is repaglinide;

the aldose reductase inhibitor is a member selected from the group consisting of zopolrestat, minalrestat, ponalrestat and tolrestat;

the insulin or insulin analog is a member selected from the group consisting of LysPro insulin, GLP-1 (7-37) insulinotropin, GLP-1 (7-36)-$NH_2$, recombinant human insulin, natural pig insulin, natural ox insulin, natural bovine insulin, natural human insulin, recombinant human argine-insulin, recombinant human aspartic-insulin, dalanated insulin, defalan insulin, glargine insulin, human insulin zinc, human insulin isophane, lispro insulin, neutral insulin and human proinsulin;

and optionally a pharmaceutically acceptable carrier or diluent.

2. The pharmaceutical composition of claim 1, wherein

X is selected from the group consisting of —O—, —S(O)$_k$—, —N($R^{11}$)—, —$CH_2$— and —C(O)—; single bond;

Y is —N($R^{12}$)—S(O)$_m$—;

wherein $R^{11}$ is hydrogen or ($C_1$-$C_8$) alkyl;

$R^{12}$ is selected from the group consisting of hydrogen and ($C_1$-$C_8$)alkyl; and the subscript m is an integer of from 0 to 2;

$R^1$ is a member selected from the group consisting of hydrogen, halogen, cyano, ($C_1$-$C_8$)alkoxy, ($C_1$-$C_8$) alkyl, —C(O)$R^{14}$, —$CO_2R^{14}$ and —C(O)N$R^{15}R^{16}$;

wherein $R^{14}$ is a member selected from the group consisting of hydrogen, ($C_1$-$C_8$)alkyl, ($C_1$-$C_8$)heteroalkyl, aryl and aryl($C_1$-$C_4$)alkyl;

$R^{15}$ and $R^{16}$ are members independently selected from the group consisting of hydrogen, ($C_1$-$C_8$)alkyl, ($C_1$-$C_8$) heteroalkyl, aryl and aryl($C_1$-$C_4$)alkyl, or taken together with the nitrogen to which each is attached form a 5-, 6- or 7-membered ring;

$R^2$ is a member selected from the group consisting of aryl and aryl($C_1$-$C_4$)alkyl; and $R^3$ is a member selected from the group consisting of halogen, cyano, ($C_1$-$C_8$)alkyl and ($C_1$-$C_8$)alkoxy.

3. The pharmaceutical composition of claim 2, wherein $Ar^1$ is a phenyl, naphthyl, benzothiazole, benzimidazole, or isoquinoline group having from 1 to 3 substituents selected from the group consisting of halogen, cyano, $CF_3$, nitro, ($C_1$-$C_8$) alkyl and ($C_1$-$C_8$)alkoxy.

4. The pharmaceutical composition of claim 1, wherein X is a divalent linkage selected from the group consisting of —O—, —C(O)—, N($R^{11}$)—, —$CH_2$— and —S(O)$_k$—.

5. The pharmaceutical composition of claim 1, where Y is —N($R^{12}$)—S(O)$_2$— wherein $R^{12}$ is hydrogen or ($C_1$-$C_8$) alkyl, and $R^2$ is a member selected from the group consisting of aryl and arylalkyl.

6. The pharmaceutical composition of claim 1, wherein $R^1$ is selected from the group consisting of hydrogen, halogen, cyano, ($C_1$-$C_8$)alkoxy, ($C_1$-$C_8$)alkyl, —C(O)$R^{14}$, —$CO_2R^{14}$ and —C(O)N$R^{15}R^{16}$ wherein $R^{14}$ is ($C_1$-$C_8$)alkyl, and $R^{15}$ and $R^{16}$ are independently selected from the group consisting of hydrogen and ($C_1$-$C_8$)alkyl, or taken together with the nitrogen to which each is attached form a 5- or 6-membered ring.

7. The pharmaceutical composition of claim 1, wherein $Ar^1$ is substituted with from one to two substituents selected from the group consisting of halogen, —$OCF_3$, —OH, —O($C_1$-$C_6$)alkyl, —$CF_3$, ($C_1$-$C_8$)alkyl and —$NO_2$.

8. The pharmaceutical composition of claim 1, wherein said compound is represented by a formula selected from the group consisting of

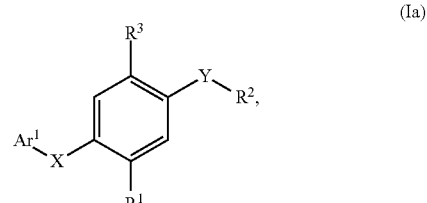

(Ia)

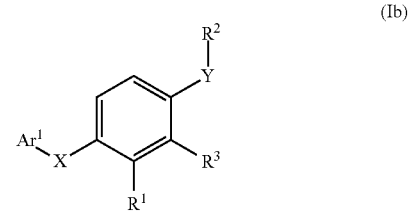

(Ib)

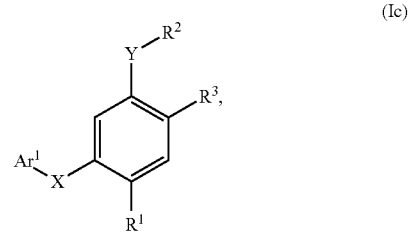

(Ic)

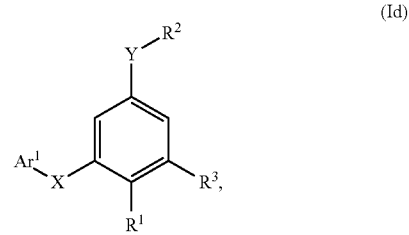

(Id)

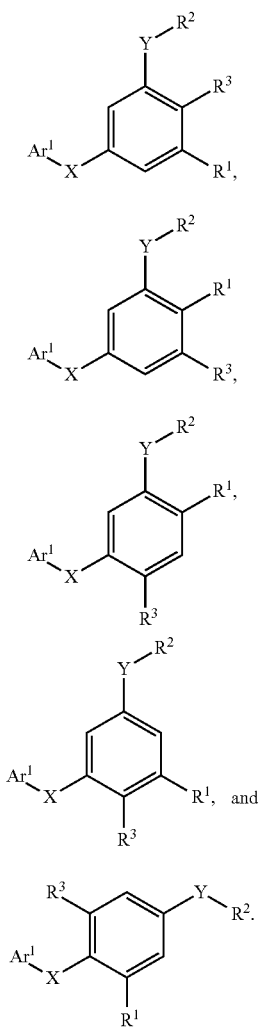

9. The pharmaceutical composition of claim 1, wherein X is a divalent linkage selected from the group consisting of —O—, —S—, —S(O)—, —S(O)$_2$—, —NH—, —CH$_2$— and —C(O)—.

10. The pharmaceutical composition of claim 1, wherein Y is —NH—S(O)$_2$— or —NH—S(O)$_2$—NH—, and R$^2$ is aryl.

11. The pharmaceutical composition of claim 1, wherein R$^2$ is selected from the group consisting of substituted phenyl, substituted pyridyl and substituted naphthyl, wherein the substituents number from one to three and are independently selected from the group consisting of halogen, —OCF$_3$, —OH, —O(C$_1$-C$_8$)alkyl, —C(O)—(C$_1$-C$_8$)alkyl, —CN, —CF$_3$, (C$_1$-C$_8$)alkyl and —NH$_2$.

12. The pharmaceutical composition of claim 1, wherein R$^1$ is selected from the group consisting of —H, halogen, C(O)R$^{14}$, —(C$_1$-C$_8$)alkyl, and —CONR$^{15}$R$^{16}$ wherein R$^{15}$ and R$^{16}$ are each independently selected from hydrogen, alkyl, aryl and arylalkyl, and R$^{14}$ is (C$_1$-C$_8$) alkyl.

13. The pharmaceutical composition of claim 1, wherein said compound of Formula (I) is selected from the group consisting of -continued

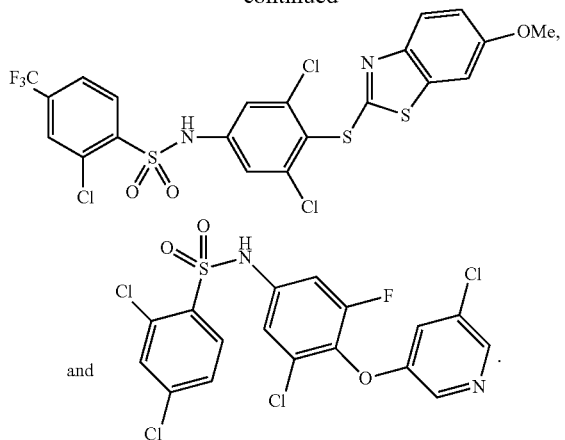

and

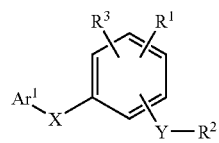

14. A pharmaceutical composition, said composition comprising:
i) a compound having the formula (I) or a pharmaceutically acceptable salt thereof:

$$Ar^1-X-\underset{R^3}{\overset{R^1}{\diagdown}}-Y-R^2 \quad I$$

wherein
Ar$^1$ is a substituted or unsubstituted quinoline group;
X is a divalent linkage selected from the group consisting of (C$_1$-C$_6$)alkylene, (C$_1$-C$_6$)alkylenoxy, (C$_1$-C$_6$)alkylenamino, (C$_1$-C$_6$)alkylene-S(O)$_k$—, —O—, —C(O)—, —N(R$^{11}$)—, —N(R$^{11}$)C(O)— and —S(O)$_k$—,
wherein
R$^{11}$ is a member selected from the group consisting of hydrogen, (C$_1$-C$_8$)alkyl, (C$_1$-C$_8$)heteroalkyl and aryl(C$_1$-C$_4$)alkyl; and the subscript k is an integer of from 0 to 2;
Y is a divalent linkage selected from the group consisting of —N(R$^{12}$)—S(O)$_m$— and —N(R$^{12}$)—S(O)$_m$—N(R$^{13}$)—;
wherein
R$^{12}$ and R$^{13}$ are members independently selected from the group consisting of hydrogen, (C$_1$-C$_8$)alkyl, (C$_1$-C$_8$)heteroalkyl and aryl(C$_1$-C$_4$)alkyl; and the subscripts m and n are independently integers of from 0 to 2;
R$^1$ is a member selected from the group consisting of hydrogen, heteroalkyl, arylalkyl, halogen, cyano, nitro, (C$_1$-C$_8$)alkyl, (C$_1$-C$_8$)alkoxy, —C(O)R$^{14}$, —CO$_2$R$^{14}$, —C(O)NR$^{15}$R$^{16}$, —S(O)$_p$—R$^{14}$, —S(O)$_q$—NR$^{15}$R$^{16}$, —O—C(O)—OR$^{17}$, —O—C(O)—R$^{17}$, —O—C(O)—NR$^{15}$NR$^{16}$, —N(R$^{14}$)—C(O)—NR$^{15}$R$^{16}$, —N(R$^{14}$)—C(O)—R$^{17}$ and —N(R$^{14}$)—C(O)—OR$^{17}$;
wherein
R$^{14}$ is a member selected from the group consisting of hydrogen, (C$_1$-C$_8$)alkyl, (C$_1$-C$_8$)heteroalkyl, aryl and aryl(C$_1$-C$_4$)alkyl;
R$^{15}$ and R$^{16}$ are members independently selected from the group consisting of hydrogen, (C$_1$-C$_8$)alkyl, (C$_1$-C$_8$)heteroalkyl, aryl and aryl(C$_1$-C$_4$)alkyl, or taken together with the nitrogen to which each is attached form a 5-, 6- or 7-membered ring;
R$^{17}$ is a member selected from the group consisting of alkyl, heteroalkyl, aryl and arylalkyl;

the subscript p is an integer of from 0 to 3; and
the subscript q is an integer of from 1 to 2; and
R$^2$ is a member selected from the group consisting of (C$_1$-C$_8$)alkyl, (C$_1$-C$_8$)heteroalkyl, aryl and aryl(C$_1$-C$_4$)alkyl; and
R$^3$ is a member selected from the group consisting of halogen, cyano, nitro, (C$_1$-C$_8$)alkyl and (C$_1$-C$_8$)alkoxy; and
ii) one or more antidiabetic agents, or pharmaceutically acceptable salts of said one or more antidiabetic agents; wherein said antidiabetic agent is a member selected from the group consisting of a sulfonylurea, an α-glucosidase inhibitor, a potassium channel antagonist, an aldose reductase inhibitor, insulin and insulin analogs, and mixtures thereof; wherein
the sulfonylurea is a member selected from the group consisting of acetohexamide, chlorpropamide, glyburide, glipizide, gliclazide, glimepiride, gliquidone, glisoxepid, glibornuride, gliamilide, glicetanile, gliflumide, glymidine, glyparamide, tolpyrramide, glyhexamide, phenbutamide, tolazamide, tolbutamide and tolcyclamide;
the α-glucosidase inhibitor is a member selected from the group consisting of acarbose, miglitol, emiglitate, voglibose, MDL-25,637, camiglibose and MDL-73,945;
the potassium channel antagonist is repaglinide;
the aldose reductase inhibitor is a member selected from the group consisting of zopolrestat, minalrestat, ponalrestat and tolrestat;
the insulin or insulin analog is a member selected from the group consisting of LysPro insulin, GLP-1 (7-37) insulinotropin, GLP-1 (7-36)-NH$_2$, recombinant human insulin, natural pig insulin, natural ox insulin, natural bovine insulin, natural human insulin, recombinant human argine-insulin, recombinant human aspartic-insulin, dalanated insulin, defalan insulin, glargine insulin, human insulin zinc, human insulin isophane, lispro insulin, neutral insulin and human proinsulin;
and optionally a pharmaceutically acceptable carrier or diluent.

15. The pharmaceutical composition of claim 14, wherein
X is selected from the group consisting of —O—, —S(O)$_k$—, —N(R$^{11}$)—, —CH$_2$— and —C(O)—;
Y is —N(R$^{12}$)—S(O)$_m$—;
wherein
R$^{11}$ is hydrogen or (C$_1$-C$_8$) alkyl;
R$^{12}$ is selected from the group consisting of hydrogen and (C$_1$-C$_8$)alkyl; and the subscript m is an integer of from 0 to 2;
R$^1$ is a member selected from the group consisting of hydrogen, halogen, cyano, (C$_1$-C$_8$)alkoxy, (C$_1$-C$_8$) alkyl, —C(O)R$^{14}$, —CO$_2$R$^{14}$ and —C(O)NR$^{15}$R$^{16}$;
wherein
R$^{14}$ is a member selected from the group consisting of hydrogen, (C$_1$-C$_8$)alkyl, (C$_1$-C$_8$)heteroalkyl, aryl and aryl(C$_1$-C$_4$)alkyl;
R$^{15}$ and R$^{16}$ are members independently selected from the group consisting of hydrogen, (C$_1$-C$_8$)alkyl, (C$_1$-C$_8$)heteroalkyl, aryl and aryl(C$_1$-C$_4$)alkyl, or taken together with the nitrogen to which each is attached form a 5-, 6- or 7-membered ring;
R$^2$ is a member selected from the group consisting of aryl and aryl(C$_1$-C$_4$)alkyl; and
R$^3$ is a member selected from the group consisting of halogen, cyano, (C$_1$-C$_8$)alkyl and (C$_1$-C$_8$)alkoxy.

16. The pharmaceutical composition of claim 14, wherein Ar$^1$ is a quinoline group having from 1 to 3 substituents selected from the group consisting of halogen, cyano, CF$_3$, nitro, (C$_1$-C$_8$)alkyl and (C$_1$-C$_8$)alkoxy.

17. The pharmaceutical composition of claim 14, wherein X is a divalent linkage selected from the group consisting of —O—, —C(O)—, N(R$^{11}$)—, —CH$_2$— and —S(O)$_k$ and a single bond.

18. The pharmaceutical composition of claim 14, where Y is —N(R$^{12}$)—S(O)$_2$— wherein R$^{12}$ is hydrogen or (C$_1$-C$_8$) alkyl, and R$^2$ is a member selected from the group consisting of aryl and arylalkyl.

19. The pharmaceutical composition of claim 14, wherein R$^1$ is selected from the group consisting of hydrogen, halogen, cyano, (C$_1$-C$_8$)alkoxy, (C$_1$-C$_8$)alkyl, —C(O)R$^{14}$, —CO$_2$R$^{14}$ and —C(O)NR$^{15}$R$^{16}$ wherein R$^{14}$ is (C$_1$-C$_8$)alkyl, and R$^{15}$ and R$^{16}$ are independently selected from the group consisting of hydrogen and (C$_1$-C$_8$)alkyl, or taken together with the nitrogen to which each is attached form a 5- or 6-membered ring.

20. The pharmaceutical composition of claim 14, wherein Ar$^1$ is substituted with from one to two substituents selected from the group consisting of halogen, —OCF$_3$, —OH, —O(C$_1$-C$_6$)alkyl, —CF$_3$, (C$_1$-C$_8$)alkyl and —NO$_2$.

21. The pharmaceutical composition of claim 14, wherein said compound is represented by a formula selected from the group consisting of

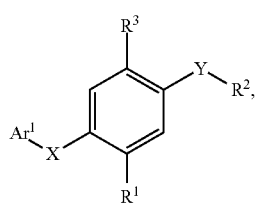
(Ia)

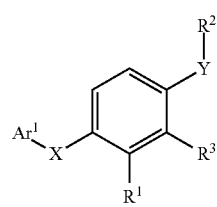
(Ib)

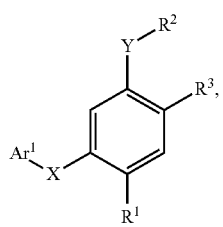
(Ic)

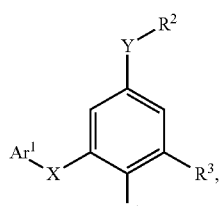
(Id)

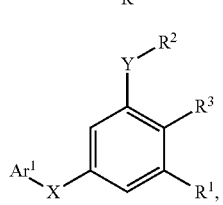
(Ie)

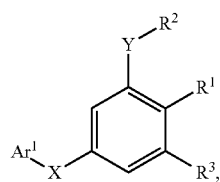
(If)

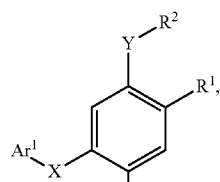
(Ig)

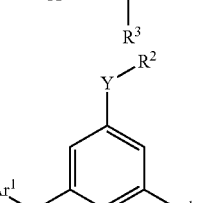
(Ih)

and

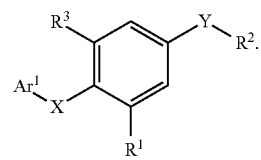
(Ii)

22. The pharmaceutical composition of claim 14, wherein X is a divalent linkage selected from the group consisting of —O—, —S—, —S(O)—, —S(O)$_2$—, —NH—, —CH$_2$— and —C(O)—.

23. The pharmaceutical composition of claim 14, wherein R$^2$ is aryl.

24. The pharmaceutical composition of claim 14, wherein R$^2$ is selected from the group consisting of substituted phenyl, substituted pyridyl and substituted naphthyl, wherein the substituents number from one to three and are independently selected from the group consisting of halogen, —OCF$_3$, —OH, —O(C$_1$-C$_8$)alkyl, —C(O)—(C$_1$-C$_8$)alkyl, —CN, —CF$_3$, (C$_1$-C$_8$)alkyl and —NH$_2$.

25. The pharmaceutical composition of claim 14, wherein R$^1$ is selected from the group consisting of —H, halogen, C(O)R$^{14}$, —(C$_1$-C$_8$)alkyl and —CONR$^{15}$R$^{16}$ wherein R$^{15}$ and R$^{16}$ are each independently selected from hydrogen, alkyl, aryl and arylalkyl, and R$^{14}$ is (C$_1$-C$_8$)alkyl.

26. The pharmaceutical composition of claim 14, wherein said compound of Formula (I) is

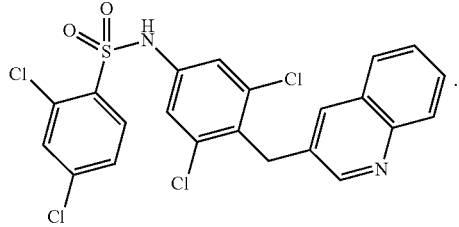

* * * * *